US011882432B2

(12) United States Patent
Shalayev et al.

(10) Patent No.: US 11,882,432 B2
(45) Date of Patent: Jan. 23, 2024

(54) PRECISION PROFESSIONAL HEALTH-RELATED (PHR) COMMUNICATION SYSTEMS AND RELATED INTERFACES

(71) Applicants: Stan G. Shalayev, Lenox, MA (US); In K. Mun, Nanuet, NY (US); Allen Kantrowitz, Williamstown, MA (US); Boris Fuchs, Dalton, MA (US)

(72) Inventors: Stan G. Shalayev, Lenox, MA (US); In K. Mun, Nanuet, NY (US); Allen Kantrowitz, Williamstown, MA (US); Boris Fuchs, Dalton, MA (US)

( * ) Notice: Subject to any disclaimer, the term of this patent is extended or adjusted under 35 U.S.C. 154(b) by 244 days.

(21) Appl. No.: 16/015,080

(22) Filed: Jun. 21, 2018

(65) Prior Publication Data
US 2019/0098492 A1 Mar. 28, 2019

Related U.S. Application Data

(60) Provisional application No. 62/522,835, filed on Jun. 21, 2017.

(51) Int. Cl.
*H04L 9/08* (2006.01)
*H04L 9/40* (2022.01)
(Continued)

(52) U.S. Cl.
CPC ............ *H04W 12/03* (2021.01); *G16H 10/60* (2018.01); *G16H 30/20* (2018.01); *G16H 40/20* (2018.01);
(Continued)

(58) Field of Classification Search
CPC .............. G06Q 50/24; G06Q 30/0273; G06Q 30/0276; G06Q 2220/00; G06Q 20/00–425; H04W 12/03; H04W 4/14; H04W 12/041; H04L 9/0819; H04L 63/0428; H04L 9/00–50; G16H 30/20; G16H 40/20; G16H 80/00; G16H 10/60
See application file for complete search history.

(56) References Cited

U.S. PATENT DOCUMENTS

2008/0133273 A1* 6/2008 Marshall ................ G06Q 10/10
705/3
2011/0125646 A1* 5/2011 Yung ...................... G16H 10/60
709/201

(Continued)

*Primary Examiner* — Ari Shahabi
(74) *Attorney, Agent, or Firm* — JWIP & Patent Services, LLC; Jacob G. Weintraub, Esq.

(57) ABSTRACT

The present invention relates to novel tools and systems that provide a precision platform for professional health-related (PHR) communication where clinical relevance is standardized for the achievement of clinical precision. In particular, the present invention provides methods, tools, and systems using precision architecture control structure (PACS) comprising professional health-related (PHR) structured dialogs suitable for precise clinical diagnosis, in combination with encrypted transmission which is capable of HIPAA compliant communication of a healthcare information system with a credentialed user. The increased clinical precision of these tools, systems, and related methods affords greater efficiency in clinical treatment that is translated into increased safety in patient care, which extends far beyond simple communication of clinically relevant information.

20 Claims, 8 Drawing Sheets

(51) Int. Cl.
  *H04W 12/03*    (2021.01)
  *G16H 30/20*    (2018.01)
  *H04W 4/14*     (2009.01)
  *G16H 40/20*    (2018.01)
  *G16H 10/60*    (2018.01)
  *G16H 80/00*    (2018.01)
  *H04W 12/041*   (2021.01)

(52) U.S. Cl.
  CPC ........... *G16H 80/00* (2018.01); *H04L 9/0819* (2013.01); *H04L 63/0428* (2013.01); *H04W 4/14* (2013.01); *H04W 12/041* (2021.01); *G06Q 2220/00* (2013.01)

(56) References Cited

U.S. PATENT DOCUMENTS

| | | | |
|---|---|---|---|
| 2011/0196704 A1* | 8/2011  | Mansour  | G06F 16/24564 |
| | | | 705/3 |
| 2013/0185098 A1* | 7/2013  | Mitchel  | G16H 10/60 |
| | | | 705/3 |
| 2015/0205550 A1* | 7/2015  | Lee      | H04N 1/00307 |
| | | | 358/1.15 |
| 2015/0206122 A1* | 7/2015  | Elliott  | G06F 16/9554 |
| | | | 705/21 |
| 2015/0220585 A1* | 8/2015  | Das      | G06F 21/6218 |
| | | | 707/741 |
| 2017/0076109 A1* | 3/2017  | Kaditz   | G06F 16/122 |
| 2017/0161439 A1* | 6/2017  | Raduchel | H04W 12/06 |
| 2018/0218126 A1* | 8/2018  | Salazar  | G16H 50/30 |
| 2018/0330825 A1* | 11/2018 | Sharifi  | G16H 50/30 |

* cited by examiner

PRECISION PROFESSIONAL HEALTH-RELATED (PHR) COMMUNICATION SYSTEMS AND RELATED INTERFACES

RELATED APPLICATIONS

This application claims priority to U.S. Provisional Patent Application No. 62/522,835 filed on Jun. 21, 2017; the entirety of which is incorporated herein by reference.

BACKGROUND OF THE INVENTION

Healthcare workers are rapidly embracing the speed and convenience afforded by electronic communication systems, such as Short Message Service (SMS) messaging systems, to improve the accuracy and efficiency of professional communication. In fact, these SMS systems are rapidly replacing pagers as a technical means of direct professional communication. However, generally, these SMS message systems are not encrypted, and hence are in direct violation of HIPAA, the federal Health Insurance Portability and Accountability Act of 1996; and to this end, patients, doctors, nurses and health care institutions are jeopardized by the burgeoning use of SMS messaging technology via open channel communications.

Fully encrypted messaging is resource intensive and would represent a significant computing burden if required at the level of the individual smart phones prior to the transmission of each individual professional health-related (PHR) communication. Although alternative messaging system platforms have been introduced for the encryption of medical data over such systems, many of these schemes have limited compliance criteria. Moreover, these messaging systems lack suitable clarity in clinical relevance to be useful in the diagnosis or treatment of patients, or to responsibly record the prescriptive activity by the medical professional.

Accordingly, there is significant need for additional tools and systems that provide a precision platform for professional health-related (PHR) communication where clinical relevance is standardized for the achievement of clinical precision.

SUMMARY OF THE INVENTION

Accordingly, the present invention is directed to novel tools and systems that provide a precision platform for professional health-related (PHR) communication where clinical relevance is standardized for the achievement of clinical precision. In particular, the present invention provides methods, tools, and systems using precision architecture control structure (PACS) comprising professional health-related (PHR) structured dialogs suitable for precise clinical diagnosis, in combination with encrypted transmission which is capable of HIPAA compliant communication of a healthcare information system with a credentialed user. The increased clinical precision of these tools, systems, and related methods affords greater efficiency in clinical treatment that is translated into increased safety in patient care, which extends far beyond simple communication of clinically relevant information.

As such, one aspect of the invention provides a precision professional health-related (PHR) communication interface comprising a machine-readable medium having instructions stored thereon for execution by a processor to perform a method. The method comprises the steps of: interfacing by a healthcare information system of a host healthcare institution with one or more wireless devices using precision architecture control structure (PACS) comprising professional health-related (PHR) structured dialogs suitable for precise clinical diagnosis; establishing one or more registries of credentialed users; assigning an encryption key to each user for use in both encryption and decryption; encrypting the PHR structured dialog prior to transmission to said wireless devices of a defined user with an assigned encryption key; and receiving the encrypted PHR structured dialog at said wireless device assigned to said user, such that the healthcare information system of the host healthcare institution is capable of communicating with one or more of said users by precision professional health-related (PHR) communication.

Another aspect of the present invention provides a precision professional health-related (PHR) communication system suitable for protecting the confidentiality and security of healthcare information within a host healthcare institution. The system comprises: a healthcare information system; one or more wireless devices; and a precision professional health-related (PHR) communication interface comprising a machine-readable medium having instructions stored thereon for execution by a processor to perform a method. The method comprises the steps of: interfacing with the healthcare information system of a host healthcare institution with one or more wireless devices using precision architecture control structure (PACS) comprising professional health-related (PHR) structured dialogs suitable for precise clinical diagnosis; establishing one or more registries of credentialed users; assigning an encryption key to each user for use in both encryption and decryption; encrypting the PHR structured dialog prior to transmission to said wireless devices of a defined user with an assigned encryption key; and receiving the encrypted PHR structured dialog at said wireless device assigned to said user, such that the healthcare information system of the host healthcare institution is capable of communicating with one or more of said users by precision professional health-related (PHR) communication. The system provides a precision communication system suitable for protecting the confidentiality and security of the professional health-related (PHR) information within the host healthcare institution.

An additional aspect of the present invention provides a method of precision professional health-related (PHR) communication. The method comprises the steps of: interfacing by a healthcare information system of a host healthcare institution with one or more wireless devices using precision architecture control structure (PACS) comprising professional health-related (PHR) structured dialogs suitable for precise clinical diagnosis; establishing one or more registries of credentialed users; assigning an encryption key to each user for use in both encryption and decryption; encrypting the PHR structured dialog prior to transmission to said wireless devices of a defined user with an assigned encryption key; and receiving the encrypted PHR structured dialog at said wireless device assigned to said user, such that the healthcare information system of the host healthcare institution is capable of communicating with one or more of said users by precision professional health-related (PHR) communication.

BRIEF DESCRIPTION OF THE DRAWINGS

Advantages of the present apparatus will be apparent from the following detailed description, which description should be considered in combination with the accompanying drawings, which are not intended limit the scope of the invention in any way.

DETAILED DESCRIPTION OF THE INVENTION

Figure 1:
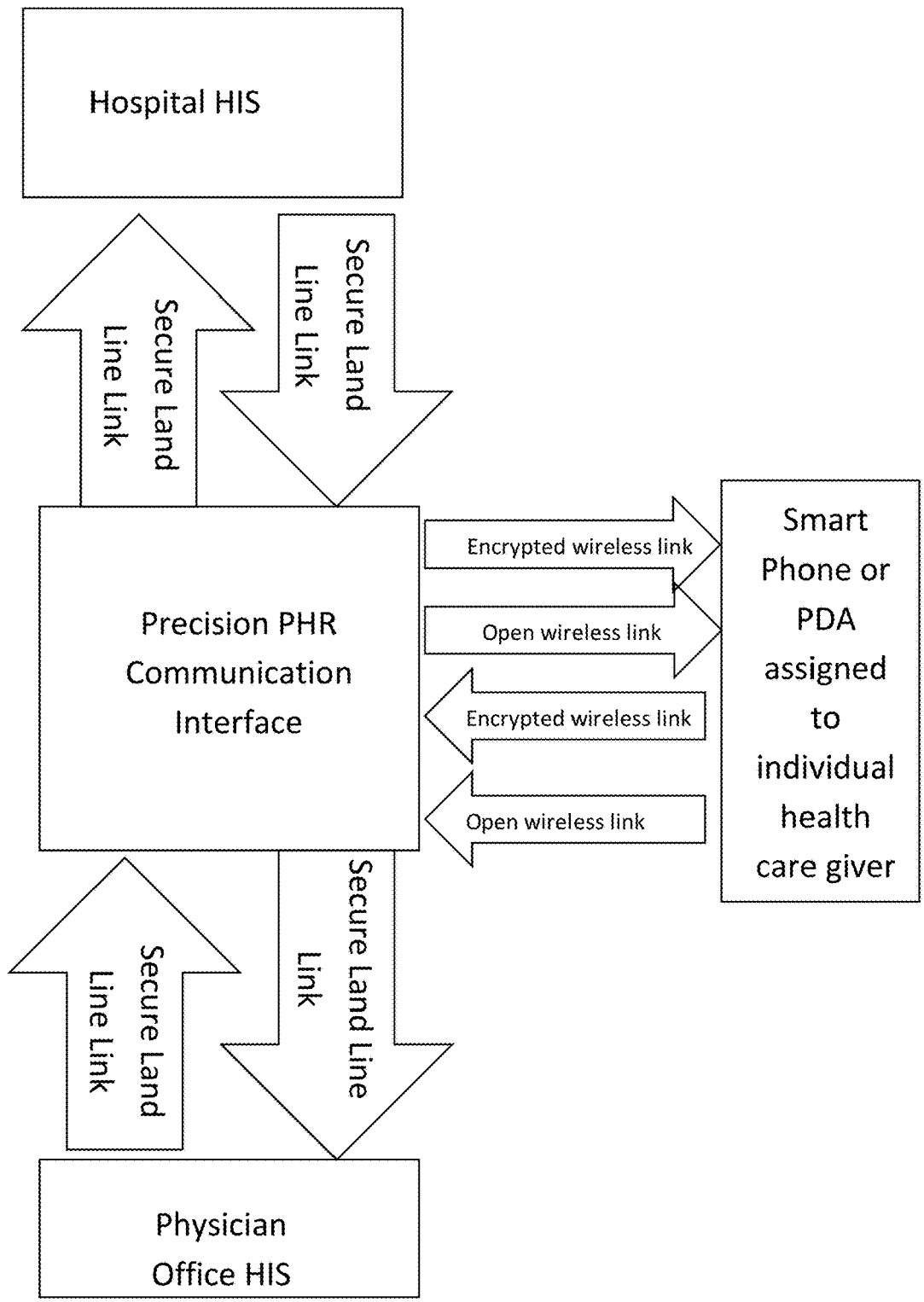
FIG. 1 depicts a schematic representation of the architecture of the core executed processes of one particular embodiment of the precision professional health-related (PHR) communication systems of the present invention.

The architecture of platforms of the present invention are designed for precision in clinically relevant profession health-related (PHR) electronic communication. In fact, the tools, incorporating systems, and the methods that support patentability employ precision architecture control structure (PACS), with optimized messaging. Such messaging comprises professional health-related (PHR) structured dialogs suitable for precise clinical diagnosis As such, the present invention is directed to novel tools and systems that provide a precision platform for professional health-related (PHR) communication where clinical relevance is standardized for the achievement of clinical precision. In particular, the present invention provides methods, tools, and systems using precision architecture control structure (PACS) comprising professional health-related (PHR) structured dialogs suitable for precise clinical diagnosis, in combination with encrypted transmission which is capable of HIPAA compliant communication of a healthcare information system with a credentialed user. The increased clinical precision of these tools, systems, and related methods affords greater efficiency in clinical treatment that is translated into increased safety in patient care, which extends far beyond simple communication of clinically relevant information. Moreover, these tools and systems also afford cost cutting measures for healthcare institutions that employ them.

The present invention, including systems, tools, and related methods will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The term "automatically" is used herein to describe a process that is automated or semi-automated. Automated processes do not contain steps that require a human operator to perform the steps. Semi-automated processes contain one or more steps that require a human operator to perform the steps; however, differ from manual processes by containing at least one step that does not require a human operator.

The language "asymmetric encryption" describes is a form of encryption where encryption keys come in pairs. In certain embodiments, the keys are interchangeable, in the sense that if key 1 encrypts a message, then 2 can decrypt it, and if key 2 encrypts a message, then key 1 can decrypt it. Asymmetric cryptography, also known as public key cryptography, uses public and private keys to encrypt and decrypt data. The keys are simply large numbers that have been paired together but are not identical (asymmetric), wherein one key in the pair can be shared with everyone; it is called the public key.

The term "blockchain," is art-recognized and is used herein to describe a distributed digital ledger where transactions (or entry into a ledger) are recorded chronologically and publicly, as a continuously growing list of records, called blocks, which are linked and secured using cryptography. A blockchain is typically managed by a peer-to-peer network collectively adhering to a protocol for inter-node communication and validating new blocks. Once recorded, the data in any given block cannot be altered retroactively without alteration of all subsequent blocks, which requires consensus of the network majority.

The language "clinical diagnosis" is used herein to describe the act of assessment of clinical factors that contribute to a clinical decision. The clinical decision may include the identification of the nature of an illness or other problem by examination of the symptoms, or the determination that more information is required and/or identify such information.

The term "dialog" as used herein the in the expression "structured dialogs" describes an electronic discussion between two or more persons, e.g., structured or defined into pre-identified precise language.

The term "encrypting" is art-recognized, and is used herein to refer to the process of protecting the security of data by using an encryption key for scrambling and unscrambling data. Encryption keys are random strings of bits designed with algorithms intended to ensure that every key is unpredictable and unique.

The language "healthcare information system" is used herein to describe any system that captures, stores, manages or transmits information related to the health of individuals or the activities of organizations that work within the health sector. In certain embodiments, such system is HIPAA compliant.

The language "healthcare institution" is used herein to describe any place, institution, building or agency (whether organized for profit or not) which provides facilities with medical services, nursing services, health screening services, other health-related services, supervisory care services, personal care services or directed care services, hospice service agencies, and in certain embodiments, includes home health agencies.

The term "HIPAA" is art-recognized, and is used herein as an abbreviation for the federal Health Insurance Portability and Accountability Act of 1996, a statute whose primary goal is to make it easier for people to keep health insurance, protect the confidentiality and security of healthcare information, and help the healthcare industry control administrative costs. In particular embodiments of the present invention, the methods of communication are HIPAA compliant with respect to their ability to maintain the confidentiality and security of healthcare information.

The term "interface" is art-recognized, and is used herein to describe a shared boundary across which two or more separate interfacing components are enabled to exchange information, which can be, for example, between: software components, computer hardware components, peripheral device components, humans and combinations thereof. Moreover, the operation of these separate components across the boundary, as in the transmission of information from the healthcare information system of a host healthcare institution to one or more wireless devices, or vice versa, is referred to herein as "interfacing." In particular embodiments, such interfacing may include authentication of a credentialed user for accessing the precision professional health-related (PHR) communication interface. In certain embodiments, the interfacing may be bi-directional. In other embodiments, the interfacing may be uni-directional. In specific embodiments, the term "interface" may be a user interface, e.g., a graphic user interface.

The language "machine-readable medium" is art-recognized, and describes a medium capable of storing data in a format readable by a mechanical device (rather than by a human). Examples of machine-readable media include magnetic media such as magnetic disks, cards, tapes, and drums, punched cards and paper tapes, optical disks, barcodes, magnetic ink characters, and solid state devices such as flash-based, SSD, etc. Machine-readable medium of the present invention are non-transitory, and therefore do not include signals per se, i.e., are directed only to hardware storage medium. Common machine-readable technologies include magnetic recording, processing waveforms, and barcodes. In particular embodiments, the machine-readable device is a solid state device. Optical character recognition (OCR) can be used to enable machines to read information available to humans. Any information retrievable by any form of energy can be machine-readable. Moreover, any data stored on a machine-readable medium may be transferred by streaming over a network. In a particular embodiment, the machine-readable medium is a network server disk, e.g., an internet server disk, e.g., a disk array. In specific embodiments, the machine-readable medium is more than one network server disk.

The language "communication channel" is art-recognized, and describes a physical transmission medium. In this respect, communicating data from one location to another requires some form of pathway or medium, and those pathways are called communication channels. In certain embodiments, communication channels might use one of two types of media: cable (twisted-pair wire, cable, and fiber-optic cable) and broadcast (microwave, satellite, radio, and infrared). Cable or wire line media use physical wires of cables to transmit data and information, while broadcast does not use wires for transmission of data and information. Moreover, open communication channels are considered non-secure pathways for communicating data.

The term "precision" is used herein to describe the characteristic of clinically effective medical communication through efficient distillation of clinically relevant standardized content. The term is meant to distinguish from ambiguous natural language that does not efficiently distill clinically relevant content, given that the ambiguity of natural non-standardized language can afford both the misexpression and misperception of clinical concepts. Such precision affords greater efficiency in clinical treatment that is translated into increased safety in patient care, which extends far beyond simple communication of clinically relevant information.

The language "professional health-related (PHR)" as used herein in reference to data and communication, describes the characteristic of data and communication being considered protected under HIPAA.

The term "SMS" is art-recognized to be an abbreviation of Short Message Service, and is also commonly referred to as a "text message". It is well-known that most cell phones support this type of text messaging, which generally offers a sender up to 160 characters to send a message to another device, and wherein longer messages are often split up into several parts.

The term "storing" is art-recognized, and is used herein to describe the act of saving data on a machine readable medium in a manner that such data is subsequently retrievable on that machine readable medium.

The term "user" is used herein to describe any person that interfaces with the tools of the present invention described herein through electronic means, e.g., computer or mobile device. Such user may be credentialed or non-credentialed, and therefore afford certain access rights in the interface based on such status. Such user, in certain embodiments, may be an administrator that is maintaining and/or customizing the interfaces or lists presented (structured dialog list, healthcare worker list, patient list).

II. Methods Precision Professional Health-Related (PHR) Communication of the Invention One embodiment of the present invention, provides a method of precision professional health-related (PHR) communication comprising the steps of:
    interfacing by a healthcare information system of a host healthcare institution with one or more wireless devices using precision architecture control structure (PACS) comprising professional health-related (PHR) structured dialogs suitable for precise clinical diagnosis;
    establishing one or more registries of credentialed users;
    assigning an encryption key to each user for use in both encryption and decryption;
    encrypting the PHR structured dialog prior to transmission to said wireless devices of a defined user with an assigned encryption key; and
    receiving the encrypted PHR structured dialog at said wireless device assigned to said user,
such that the healthcare information system of the host healthcare institution is capable of communicating with one or more of said users by precision professional health-related (PHR) communication.

In certain embodiments of the present invention, the method further comprises the step of transmission of the encrypted PHR structured dialog to said wireless devices of the defined user with an assigned encryption key. Such transmission may occur over any open channel communication, e.g., SMS.

In certain embodiments of the present invention, the method further comprises the step of transmission of an encrypted PHR structured dialog from said wireless device assigned to said user to the healthcare information system. Such transmission may occur over any open channel communication, e.g., SMS.

In certain embodiments of the present invention, the method further comprises the step of acknowledgement of receipt of the encrypted PHR structured dialog. In particular embodiments, the acknowledgement is an automatic acknowledgment of technical receipt of message, e.g., which may be generated by the interface on the side of the receiver, and creates an audit trail of the message. In particular embodiments, the acknowledgement is a distinct second order acknowledgment that is the clinical (user generated) acknowledgment. In certain embodiments, if either the first technical acknowledgment or the second order clinical acknowledgement is not sent, the encrypted PHR structured dialog will be resent according to pre-specified rules or the sender will be notified of the missing acknowledgement. In specific embodiments, the sender is capable of specifying the retransmission rules, e.g., at the time of construction of the encrypted PHR structured dialog.

In certain embodiments of the present invention, the method further comprises the step of transmission of non HIPAA related communications, which may be unencrypted. In particular embodiments, the method further comprises the storage/archiving thereof.

In certain embodiments of the present invention, the method further comprises the step of storage of PHR data, e.g., an encrypted PHR structured dialog to/from said wireless device assigned to said user or response thereto. Such stored data may also form the basis for audit trail recording. In particular embodiments, the stored data may form part of an electronic medical records (EMR) system, affording access to the stored data to both credentialed and non-credentialed users, i.e., all users who have access to the EMR system database. In specific embodiments, storage and archiving are performed in accordance with hospital specific policies (e.g., patient ID linked; hospital records; provider ID; and optional access within specified period of time for medical legal).

In certain embodiments of the present invention, the integrity of the stored PHR data may be additionally protected using blockchain, which by design, is resistant to modification of the data, and can be proactively utilized for auditing and reanalyzing value of clinical messages via AI process. In certain embodiments, the blockchain used in the present invention is managed by a peer-to-peer network collectively adhering to a protocol for inter-node communication among credentialed users, which are capable of validating new blocks, including but not limited to global and local healthcare systems, hospital based platforms and systems, medical providers, medical teams, inpatient and outpatient facilities, pharmacies, insurance companies exchanges, biotechnology and pharmaceutical business entities. In particular embodiments, predictive learning (e.g., with artificial intelligence, e.g., using continuous stream of matrix analytical analysis to accurately determine outliers and by design to improve viability and utility of clinical messaging via verification of blockchain adhered protocol data) may be used for directionally vectoring diagnosis to advance the precision of the methods, interfaces and systems of the present invention.

In certain embodiments of the present invention, the method further comprises the step of haptic feedback to a user upon interfacing with a graphical user interface, for use in procedure related environments, e.g., emergency rooms, Operating Room (OR), etc. (employing, for example, sterile covers for smart devices, e.g., smartphones, as option for continuous system utilization)

The methods of the present invention are useful as instructions stored on a machine-readable medium for execution by a processor to perform the method. In certain embodiments, the methods and tools of the present invention also make use and/or comprise a processor. Accordingly, any methods of the present invention, alone or in combination with other methods (such as those described herein or elsewhere) may be stored on a machine-readable medium for execution by a processor to perform the method. Such a composition comprises an interfacing tool of the invention, i.e., a precision professional health-related (PHR) communication interface.

As such, an additional embodiment of the present invention provides an interfacing tool comprising a machine-readable medium having instructions stored thereon for execution by a processor to perform any method of precision professional health-related (PHR) communication described herein, e.g., which may be used to interface, communicate, and/or transmit precision PHR data/structured dialog between a healthcare information system of a host healthcare institution and credentialed users (e.g., doctors, nurses, and other healthcare workers).

In certain embodiments of the interfacing tools of the present invention, the method further comprises presenting a user interface (e.g., a graphical user interface (GUI)) to a user that is designed to facilitate certain actions selected from the group consisting of interfacing by a healthcare information system of a host healthcare institution with one or more wireless devices using precision architecture control structure (PACS) comprising professional health-related (PHR) structured dialogs suitable for precise clinical diagnosis; establishing one or more registries of credentialed users; assigning an encryption key to each user for use in both encryption and decryption; encrypting the PHR structured dialog prior to transmission to said wireless devices of a defined user with an assigned encryption key; and receiving the encrypted PHR structured dialog at said wireless device assigned to said user. In particular embodiments, the method further comprises interfacing with the user interface by the user. In particular further embodiments, the method comprises storing said collected data/structured dialog on a server (e.g., capable of access or modification). In specific embodiments, one or more of these steps may be automated.

In certain embodiments of the precision professional health-related (PHR) communication interface of the present invention, the machine-readable medium is online software. In a particular embodiment, the software is an online application. In particular embodiments, the software is a web-based application. In an alternative particular embodiment, the software is a cloud-based application. Moreover, the interfacing tool may be a web application accessible in an Internet browser, desktop software running on Windows, Mac OS, Linux (or any other operating system), or a mobile application (available on smart devices, e.g., smartphones, or tablets) In particular embodiments, the communication interface is a cloud based interface, e.g., based on iOS or Android platforms. In particular embodiments, the PHR communication interface transmits and/or receives the transmitted PHR structured dialog as an SMS text message, i.e., in a separate conventional text message application, which is then imported into the PHR communication interface. In specific embodiments, the precision professional health-related (PHR) communication interface (e.g., application)

requests permission to view messages received by an SMS application, and the interface is alerted to activate upon receipt by the SMS application of a sequence resulting in interface activation, i.e., wakes up the app based on the activation by a sequence received in the SMS application.

In certain embodiments of the precision professional health-related (PHR) communication interface of the present invention, the machine-readable medium is selected from the group consisting of magnetic media, punched cards, paper tapes, optical disks, barcodes, magnetic ink characters, and solid state devices, e.g., one or more network server disks.

In another embodiment, the present invention provides a method for the healthcare institution to monitor and log the open SMS traffic detected in the airwaves in a location for auditing and management purposes. Such a monitoring program would be expected to encourage the healthcare workers to utilize a private application HIPAA-compliant message system to transmit PHR communications rather than a conventional SMS application A. Interfacing with Healthcare Information System of Host Healthcare Institution In one step of the method, the step provides for interfacing by a healthcare information system of a host healthcare institution with one or more wireless devices using precision architecture control structure (PACS) comprising professional health-related (PHR) structured dialogs suitable for precise clinical diagnosis. In certain embodiments, the healthcare information system of the host healthcare institution maintains a central registry of credentialed users selected from healthcare workers and a registry of currently active patients. In alternative embodiments, the central registry of credentialed users is maintained on a machine-readable medium, e.g., a server, separate from the healthcare information system.

The communication platform for use with the wireless devices using precision architecture control structure may be selected from any open channel communication platform where mobile devices are able communicate wirelessly, including by radio signals such as cellular signal, Wi-Fi, or Bluetooth, or any other communication means that affords transmission of data without wires from one point to another, and is capable of ensuring the integrity of the wirelessly transmitted communication data, e.g., maintaining HIPAA compliance. In certain embodiments, the wireless devices are selected from the group consisting of mobile/cellular telephones (e.g., smart devices, e.g., smartphones), tablets, desktop computers, laptop computers, notebook computers, and medical equipment (e.g., medical devices used in the treatment, prevention, and diagnosis of a patient). In certain embodiments, the identity of the medical equipment that is capable of wireless transmission is also maintained in the central registry as a credentialed user.

The methods of precision professional health-related (PHR) communication provide for interfacing with one or more credentialed users through an interfacing tool, e.g., on a server. The interfacing tools of the present invention are user interfaces for providing precision professional health-related (PHR) communication, e.g., graphical user interfaces (GUI), which are user-facing for interacting with a credentialed user to transmit information, collect information, as well as act on that information through combination, analysis, and ultimately providing diagnostic analysis through precision PHR communication. In particular embodiments, such interface may comprise interface components/modules such as buttons, drop-down menus, drop-down lists, entry blanks, links to prior stored information, and text for: instruction, request, or stored information. Moreover, such interface components/modules and list members, e.g., healthcare workers or patient names, may be updated/modified (e.g., by an administrator of the interface or in an automated fashion by reference to separate listing held outside the interface, e.g., in the EMR system).

In certain embodiments of the invention, the interface visualization may provide for depicting timelines, e.g., in landscape view, with several parallel processes.

In certain embodiments of the invention, the interface may be patient centered to establish optimal team involvement.

In certain embodiments of the invention, the interface visualization may provide for visualizing team members availability at a given time (e.g., which may be engaged automatically). In particular embodiments, such visualization may be filtered by time and team member.

In certain embodiments of the invention, the step of interfacing with the healthcare information system of the host healthcare institution comprises authentication of the credentialed user for accessing the communication interface. In certain embodiments, to access the precision architecture control structure (PACS), the credentialed user may first download an app, or access a web browser or web portal. In particular embodiments, registration or authentication (e.g., single or multi factor authentication, e.g., signing in via password) is required prior to utilization of the precision professional health-related (PHR) communication interface. In particular embodiments, the user registers with an administrator of the healthcare information system of the host healthcare institution, e.g., creating a unique interface with a particular encryption key.

In certain embodiments of the invention, the step of interfacing with the healthcare information system of the host healthcare institution comprises creation of a patient specific storage path, e.g., incident specific storage path, e.g., injury specific storage path, to collect the professional health-related (PHR) data (e.g., structured dialogs) from a user, e.g., credentialed user. In particular embodiments, the patient specific storage path is based on the healthcare worker. In specific embodiments, the patient specific storage path is based on a team of healthcare workers.

In certain embodiments of the invention, the step of interfacing with the healthcare information system of the host healthcare institution comprises reestablishing interface with an existing patient specific storage path to collect additional data, e.g., PHR data, e.g., structured dialogs. In particular embodiments, the existing patient specific storage path is based on the healthcare worker. In specific embodiments, the existing patient specific storage path is based on the incident. In certain embodiments, the existing patient specific storage path is created by the healthcare worker. In certain embodiments, the existing patient specific storage path is created by the administrator of the communication interface, e.g., based on credentialed users and structured dialogs.

In certain embodiments of the invention, the one or more wireless devices interfacing with the healthcare information system of a host healthcare institution also interfaces with one or more additional healthcare information systems (e.g., wherein the first is a hospital healthcare information system and the second is a physician office healthcare information system.

i. Precision Architecture Control Structure (PACS)

The precision architecture control structure (PACS) of the present invention comprises professional health-related (PHR) structured dialogs suitable for precise clinical diagnosis, including in certain embodiments, for example, clinical treatment options. In particular, the present invention provides methods, tools, and systems using precision architecture control structure (PACS) comprising professional health-related (PHR) structured dialogs suitable for precise clinical diagnosis, in combination with encrypted transmission which is capable of HIPAA compliant communication of a healthcare information system with a credentialed user. The increased clinical precision of these tools, systems, and related methods affords greater efficiency in clinical treatment that is translated into increased safety in patient care.

The PACS of the present invention comprises a database of structured dialog alternatives that afford unique precision to PHR communication among credentialed users using discrete level messaging, aggregate level messaging, and super-aggregate messaging. The precision of the structured dialogs derives, at its core, from discrete level messaging directed to primitive events and the standardized precise capture/representation of those events through selection from a pre-identified database listing. Discrete level messaging includes, but is not limited to, the capture of basic analytical dialogs and data entry for measurements, observations, and other data points that instruct the credentialed user precisely on basic analytical data useful for developing a diagnosis. Discrete level messaging aggregation may be utilized to advance the structured dialog progression in a given dialog resulting in aggregate level messaging. Aggregate level messaging introduces more advanced analytical considerations into the structured dialogs, as well as certain basic diagnoses. In particular embodiments, predictive learning (e.g., with artificial intelligence, e.g., using analytical analysis to accurately determine outliers) may be used to aggregate the discrete level messaging of the PACS to result in aggregate level messaging. In certain further embodiments, the aggregate level messaging is further aggregated to advance the structured dialog progression in a given dialog resulting in super-aggregate level messaging. Such super-aggregate level messaging is directed to a diagnosis based on both discrete level messaging and aggregate level messaging.

In certain embodiments of the PACS of the present invention, medical equipment may produce discrete level messaging, for example, patient thermometer measurements. Such patient measurements may be transmitted manually or through automated means from the medical equipment registered as a credentialed user, as a structured dialog comprising the discrete level messaging to a credentialed user (e.g., a person or medical equipment registered as a credentialed user) and/or recorded in a database, e.g., an EMR system (e.g., for diagnostic or administrative purposes such as billing). In certain embodiments, the structured dialog is first passed to the healthcare information system of the host healthcare institution and then passed to the credentialed user, e.g., wherein the healthcare institution may be used as the intermediary gate of structured dialogs (e.g., which may, in turn, be used to parse relevant information to and from the EMR). In particular embodiments, the discrete level messaging may be logged into a relational database designed to establish follow-up action or for combination with other discrete level messaging, resulting in aggregate level diagnosis and super-aggregate level diagnosis (i.e., from the combination of aggregate level messaging in the same platform), for example, via automation. In specific embodiments, the automated detection of a diagnosis may be used for triage purposes, e.g., generating a warning, e.g., a critical warning. In certain specific embodiments, the prioritization of the messaging may be defined by hospital policies and provider specific requirement.

In certain embodiments of the PACS of the present invention, the discrete, aggregate, and super-aggregate messaging of the structured dialogs may be grouped with color coded changes, e.g., progressive color coded changes. For example, color changes may depict the urgency of the response time or are in compliance with hospital policies. In particular embodiments the PACS of the present invention may be presented through additional characterization (other than by color) for color blind users, for example, through utilization of different shapes instead of color (e.g., hospital specific), e.g., 1 to 3 stars or traveling star shape.

In certain embodiments the structured dialogs are presented in a manner that the credentialed user may select from a list (e.g., a pop-up list, a checklist, a scrolling list, a drop-down list, any other iteration of generated list, for example, known in the state of art). For example, when a credentialed user, such as an individual healthcare worker, wishes to transmit a PHR communication, a private application is launched on a suitable mobile device, e.g., a smart device, e.g., smartphone, which presents a user interface that allows the simple and rapid assembly of a PHR communication by presenting a list of options to engage in structured dialog.

In certain embodiments of the PACS of the present invention, the PACS comprises an interface feature allowing the ability of the credentialed user to enter any text, i.e., "free text." In particular embodiments, the PACS further comprises the step of screening and/or auditing this additional free text for HIPAA-sensitive content. In particular embodiments, the PACS further comprises the step of screening and/or auditing this additional free text for relation to existing/stored structured dialog options, i.e., mapping the free text language to existing structured dialog. Moreover, stored free text, e.g., maintained by the healthcare information system, creates an opportunity to iteratively refine the menu of available structured dialog options. An alternative embodiment provides each credentialed user, e.g., a healthcare worker, the ability to update/customize a personal registry of structured dialog messages in the healthcare information system of the host healthcare institution. In specific embodiments, the healthcare information system of the host healthcare institution distributes to every credentialed user the updated/customized structured dialog entered by other credentialed users, e.g., through a centralization of the structured dialog options (e.g., as either encrypted or unencrypted). In specific embodiments, free text may be entered using voice recognition input, for increased speed/efficiency. Moreover, in additional embodiments, the PACS may be analyzed for free text to characterize compliance with the precision aspects of the invention, e.g., in real-time. In specific embodiments, the interface may provide a report on the provider or team member related to this analysis, e.g., to optimize utilization of structured dialogs by team members (e.g., in a feedback loop, e.g., infinite loop).

In certain embodiments of the present invention, recognition of repetitive activity, structured dialogs, and/or free text may be used to optimize routine tasks, e.g., across all users or for an individual user. In particular embodiments, repetitive activity, structured dialogs, and free text may be analyzed in real time to provide improved interfacing with an individual user.

In certain embodiments of the PACS of the present invention, the PACS provides the opportunity to record free text, e.g., in a dialog entry box. In certain embodiments, the PACS provides dialog anticipation text for offering suggestions to the credentialed user. In particular embodiments, the predictive anticipation aligns/maps the free text to a structured dialog.

B. Establishing One or More Registries of Credentialed Users,

Another step of the methods of precision professional health-related (PHR) communication of the present invention comprises establishing one or more registries of credentialed users. Credentialed users may be selected from the group consisting of healthcare workers, patients e.g., active patients, medical equipment, and any combination thereof. Such healthcare workers are medical professionals (e.g., doctor, nurse, pharmacist, etc.) suitable for collecting, distributing, and receiving PHR data/information.

In certain embodiments of the present invention, the credentialed user is selected from medical equipment, a healthcare worker, or an active patient.

In certain embodiments of the present invention, the credentialed user is selected from a healthcare worker or an active patient.

In certain embodiments of the present invention, the credentialed user is selected from medical equipment. In particular embodiments, the medical equipment is selected from machines included from but not limited to generating patient specific physiological data, hospital medical equipment, and hospital ancillary equipment. Such equipment is capable of generating discrete level messaging, aggregate level messaging, and super-aggregate messaging. Discrete level messaging includes status information related to the machine, availability and resource allocation/identification including equipment, personnel, and diagnostic resources. In specific embodiments, the medical equipment is capable of interfacing with the Internet of Things.

In certain embodiments of the present invention, the host healthcare institution maintains the central registry of credentialed users. In certain embodiments, each credentialed user is assigned a code reference related to encryption keys, and therefore provided access to the professional health-related communication/information. In particular embodiments, the host healthcare institution distributes an application to the smart phones assigned to each health care worker.

In certain embodiments of the present invention, the healthcare worker (e.g., doctors and/or registered nurses) is assigned, e.g., as a team, to a patient. In certain embodiments, this team roster may be assigned upon creation of a patient registry listing. In certain embodiments, this team roster may be assigned/presented at time of communication, e.g., structured dialog creation, to define message recipient(s), and can optionally accommodate cross-coverage relationships. Also, the history of the care team membership roster can be stored, e.g., to determine who is on a previous shift or on next shift.

In certain embodiments of the registry, each patient has an associated table specifying, for example: Patient ID (e.g., name, patient government issue ID, patient specific number, MR (medical record) number, i.e., part of two tier number system), and current location such as inpatient bed or outpatient status); family members; contact phone numbers of patient and family; health care team including PCP; specialists; nurses; respiratory therapy; physical therapy; occupational therapy; speech therapy; and possible: med reconciliation list.

In certain embodiment of the invention, the registry of credentialed users is stored on the healthcare information system of the host healthcare institution (e.g., capable of access or modification).

In certain embodiment of the invention, the registry of credentialed users is stored on a machine readable medium, e.g., server, separate from the healthcare information system of the host healthcare institution (e.g., capable of access or modification).

In certain embodiments, to access the precision architecture control structure (PACS), the credentialed user may first download an app, or access a web browser or web portal. In particular embodiments, registration or authentication (e.g., single or multi factor authentication, e.g., signing in via password) is required prior to utilization of the precision professional health-related (PHR) communication interface. In particular embodiments, the user registers with an administrator of the healthcare information system of the host healthcare institution, e.g., creating a unique interface with a particular encryption key.

C. Assigning Encryption Key to Each User for Use in Encryption and Decryption

In another step of the methods of precision professional health-related (PHR) communication of the present invention, the method comprises assigning an encryption key to each user for use in both encryption and decryption. Such encryption affords HIPAA compliance to these methods. In certain embodiments, encryption provides a multi-tiered distributed HIPAA-compliant asymmetric encryption method.

Encryption keys are designed with algorithms intended to ensure that every key is unpredictable and unique, e.g., a random string of bits created explicitly for scrambling and unscrambling data. Asymmetric encryption is a form of encryption where keys come in pairs. In certain embodiments, the keys are interchangeable, in the sense that if key 1 encrypts a message, then 2 can decrypt it, and if key 2 encrypts a message, then key 1 can decrypt it. Asymmetric cryptography, also known as public key cryptography, uses public and private keys to encrypt and decrypt data. The keys are simply large numbers that have been paired together but are not identical (asymmetric). One key in the pair can be shared with everyone, and it is called the public key. Moreover, upon assignment of an encryption key to a user, PHR communications may be transmitted using non-secure communication channels, such as SMS.

In certain embodiments of the invention, assigning an encryption key to each user utilizes a public-key asymmetric encryption algorithm. In particular embodiments, the healthcare information system transmits to the smart device, e.g., smartphone, application an encrypted list of healthcare worker names and randomly-assigned health care worker code numbers.

In certain embodiments of the invention, assigning an encryption key to each user utilizes a public-key asymmetric encryption algorithm. In particular embodiments, the healthcare information system transmits to the smart device, e.g., smartphone, application, in a HIPPA-compliant fashion, an encrypted list of patient names and randomly-assigned patient code numbers.

In certain embodiments of the invention, assigning an encryption key to each user utilizes a public-key asymmetric encryption algorithm, wherein the structured dialogs are encrypted before transmission by healthcare information system of the host healthcare institution to the smart device, e.g., smartphone, application together with randomly assigned code numbers.

D. Encrypting PHR Structured Dialog Prior to Transmission to Wireless Devices of Defined User with Assigned Encryption Key In another step of the methods of precision professional health-related (PHR) communication of the present invention, the method comprises encrypting the PHR structured dialog prior to transmission to said wireless devices of a defined user with an assigned encryption key. Applying the encryption key to the transmission of each user, prior to the transmission, affords the ability to transmit the communication using non-secure, open communication channels, such as SMS (i.e., as the random numbers assigned by the encryption to the recipient, the patient and the structured dialog cannot be understood by direct inspection). In particular embodiments, free text used, e.g., in addition to the structured dialogs, is also encrypted using the same encryption process.

Further, certain embodiments of the methods of the invention provide for analysis of the communication for HIPAA protected content. In particular embodiments, communication of information that is not HIPAA protected may occur over open channel without encryption (e.g., unless HIPAA characterized information is communicated, such as patient ID or patient related data, subjecting all communication to be considered as part of the medical records).

In certain embodiments of the invention, the encryption is achieved by using a public-key asymmetric encryption algorithm with computing resource needs such that the major computing burden is placed on the encryption process and a minor computing burden is placed on the decryption process.

E. Receiving Encrypted PHR Structured Dialog at Wireless Device Assigned to User Another step of the methods of precision professional health-related (PHR) communication of the present invention, the method comprises receiving the encrypted PHR structured dialog at said wireless device assigned to said user, e.g., healthcare worker. When the PHR structured dialog is received by the smart device (e.g., smartphone) assigned to the 'destination' healthcare worker, the private application converts the coded PHR structured dialog by substituting plain-text for the coded messages using a decryption key, thereby revealing the full intended message. The coded, or encrypted, structured dialog may be received via non-secure communication channels, e.g., SMS; which may then be imported by the smart device communication interface for action by the communication interface.

In certain embodiments of the present invention, the encrypted PHR structured dialog is decrypted into user viewable information, e.g., plain-text, thereby revealing the full intended structured dialog.

In certain embodiments of the present invention, the encrypted PHR structured dialog is decrypted to create a medical history log, e.g., in an EMR.

In certain embodiments of the present invention, the encrypted PHR structured dialog is decrypted to initiate an automated aggregate level (or super-aggregate level) response action, e.g., creating a warning response. Such response may include, for example, scheduling actions to make efficient use of resources. In particular embodiments, such warnings may be captured to identify trends and afford predictive needs for medical equipment.

In certain embodiments, the receipt of the encrypted PHR structured dialog at said wireless device assigned to the user begins a response period that may be defined/classified as non-urgent or urgent. Such definition/classification may assist in the act of triage of a patient condition. In certain embodiments, the communication may require an instant response. In particular embodiments, the importance and urgency may be reflected using measures selected from the group consisting of a countdown, visual field within messaging system, availability to the healthcare worker/team until completion, and any combination thereof. For example, importance and urgency may be reflected by implementation of flag system for priority and visual confirmation with default halt and switch to cross coverage if progression of non-responded and unconfirmed messages reaches a critical hospital specific number, and/or other set parameters and criteria are not met.

III. Precision Professional Health-Related (PHR) Communication Interfaces of the Invention The methods of the present invention are useful as instructions stored on a machine-readable medium for execution by a processor to perform the method. In certain embodiments, the methods and tools of the present invention also make use and/or comprise a processor. Accordingly, any methods of the present invention, alone or in combination with other methods (such as those described herein or elsewhere) may be stored on a machine-readable medium for execution by a processor to perform the method. Such a composition comprises an interfacing tool of the invention, i.e., a precision professional health-related (PHR) communication interface.

In this respect, the methods of precision professional health-related (PHR) communication provide for interfacing with one or more credentialed users through an interfacing tool, e.g., on a server. The interfacing tools of the present invention are user interfaces for providing precision professional health-related (PHR) communication, e.g., graphical user interfaces (GUI), which are user-facing for interacting with a credentialed user to transmit information, collect information, as well as act on that information through combination, analysis, and ultimately providing diagnostic analysis through precision PHR communication.

One embodiment of the present invention provides a precision professional health-related (PHR) communication interface comprising a machine-readable medium having instructions stored thereon for execution by a processor to perform a method comprising the steps of:

interfacing by a healthcare information system of a host healthcare institution with one or more wireless devices using precision architecture control structure (PACS) comprising professional health-related (PHR) structured dialogs suitable for precise clinical diagnosis;

establishing one or more registries of credentialed users;

assigning an encryption key to each user for use in both encryption and decryption;

encrypting the PHR structured dialog prior to transmission to said wireless devices of a defined user with an assigned encryption key; and receiving the encrypted PHR structured dialog at said wireless device assigned to said user, such that the healthcare information system of the host healthcare institution is capable of communicating with one or more of said users by precision professional health-related (PHR) communication.

In certain embodiments of the interfaces of the present invention, the method further comprises the step of transmission of the encrypted PHR structured dialog to said wireless devices of the defined user with an assigned encryption key. Such transmission may occur over any open channel communication, e.g., SMS.

In certain embodiments of the interfaces of the present invention, the method further comprises the step of transmission of an encrypted PHR structured dialog from said wireless device assigned to said user to the healthcare information system. Such transmission may occur over any open channel communication, e.g., SMS.

In certain embodiments of the interfaces of the present invention, the method further comprises the step of acknowledgement of receipt of the encrypted PHR structured dialog. In particular embodiments, the acknowledgement is an automatic acknowledgment of technical receipt of message, e.g., which may be generated by the interface on the side of the receiver, and creates an audit trail of the message. In particular embodiments, the acknowledgement is a distinct second order acknowledgment that is the clinical (user generated) acknowledgment. In certain embodiments, if either the first technical acknowledgment or the second order clinical acknowledgement is not sent, the encrypted PHR structured dialog will be resent according to pre-specified rules or the sender will be notified of the missing acknowledgement. In specific embodiments, the sender is capable of specifying the retransmission rules, e.g., at the time of construction of the encrypted PHR structured dialog.

In certain embodiments of the interfaces of the present invention, the method further comprises the step of transmission of non HIPAA related communications, which may be unencrypted. In particular embodiments, the method further comprises the storage/archiving thereof.

In certain embodiments of the interfaces of the present invention, the method further comprises the step of storage of PHR data, e.g., an encrypted PHR structured dialog to/from said wireless device assigned to said user or response thereto. Such stored data may also form the basis for audit trail recording. In particular embodiments, the stored data may form part of an electronic medical records (EMR) system, affording access to the stored data to both credentialed and non-credentialed users, i.e., all users who have access to the EMR system database. In specific embodiments, storage and archiving are performed in accordance with hospital specific policies (e.g., patient ID linked; hospital records; provider ID; and optional access within specified period of time for medical legal).

In certain embodiments of the interfaces of the present invention, the integrity of the stored PHR data may be additionally protected using blockchain, which by design, is resistant to modification of the data, and can be proactively utilized for auditing and reanalyzing value of clinical messages via AI process. In certain embodiments, the blockchain used in the present invention is managed by a peer-to-peer network collectively adhering to a protocol for inter-node communication among credentialed users, which are capable of validating new blocks, including but not limited to global and local healthcare systems, hospital based platforms and systems, medical providers, medical teams, inpatient and outpatient facilities, pharmacies, insurance companies exchanges, biotechnology and pharmaceutical business entities. In particular embodiments, predictive learning (e.g., with artificial intelligence, e.g., using continuous stream of matrix analytical analysis to accurately determine outliers and by design to improve viability and utility of clinical messaging via verification of blockchain adhered protocol data) may be used for directionally vectoring diagnosis to advance the precision of the methods, interfaces and systems of the present invention.

In certain embodiments of the interfaces of the present invention, the method further comprises the step of haptic feedback to a user upon interfacing with a graphical user interface, for use in procedure related environments, e.g., emergency rooms, Operating Room (OR), etc. (employing, for example, sterile covers for smart devices, e.g., smartphones, as option for continuous system utilization)

In certain embodiments of the interfaces of the present invention, the method further comprises presenting a user interface (e.g., a graphical user interface (GUI)) to a user that is designed to facilitate certain actions selected from the group consisting of interfacing by a healthcare information system of a host healthcare institution with one or more wireless devices using precision architecture control structure (PACS) comprising professional health-related (PHR) structured dialogs suitable for precise clinical diagnosis; establishing one or more registries of credentialed users; assigning an encryption key to each user for use in both encryption and decryption; encrypting the PHR structured dialog prior to transmission to said wireless devices of a defined user with an assigned encryption key; and receiving the encrypted PHR structured dialog at said wireless device assigned to said user. In particular embodiments, the method further comprises interfacing with the user interface by the user. In particular further embodiments, the method comprises storing said collected data/structured dialog on a server (e.g., capable of access or modification). In specific embodiments, one or more of these steps may be automated.

In certain embodiments of the precision professional health-related (PHR) communication interface of the present invention, the machine-readable medium is online software. In a particular embodiment, the software is an online application. In particular embodiments, the software is a web-based application. In an alternative particular embodiment, the software is a cloud-based application. Moreover, the interfacing tool may be a web application accessible in an Internet browser, desktop software running on Windows, Mac OS, Linux (or any other operating system), or a mobile application (available on smart devices, e.g., smartphones, or tablets) In particular embodiments, the communication interface is a cloud based interface, e.g., based on iOS or Android platforms. In particular embodiments, the PHR communication interface transmits and/or receives the transmitted PHR structured dialog as an SMS text message, i.e., in a separate conventional text message application, which is then imported into the PHR communication interface. In specific embodiments, the precision professional health-related (PHR) communication interface (e.g., application) requests permission to view messages received by an SMS application, and the interface is alerted to activate upon receipt by the SMS application of a sequence resulting in interface activation, i.e., wakes up the app based on the activation by a sequence received in the SMS application.

In certain embodiments of the precision professional health-related (PHR) communication interface of the present invention, the machine-readable medium is selected from the group consisting of magnetic media, punched cards, paper tapes, optical disks, barcodes, magnetic ink characters, and solid state devices, e.g., one or more network server disks.

A. Interfacing with Healthcare Information System of Host Healthcare Institution In one step of the method, the step provides for interfacing by a healthcare information system of a host healthcare institution with one or more wireless devices using precision architecture control structure (PACS) comprising professional health-related (PHR) structured dialogs suitable for precise clinical diagnosis. In certain embodiments, the healthcare information system of the host healthcare institution maintains a central registry of credentialed users selected from healthcare workers and a registry of currently active patients. In alternative embodiments, the central registry of credentialed users is maintained on a machine-readable medium, e.g., a server, separate from the healthcare information system.

The communication platform for use with the wireless devices using precision architecture control structure may be selected from any open channel communication platform where mobile devices are able communicate wirelessly, including by radio signals such as cellular signal, Wi-Fi, or Bluetooth, or any other communication means that affords transmission of data without wires from one point to another, and is capable of ensuring the integrity of the wirelessly transmitted communication data, e.g., maintaining HIPAA compliance. In certain embodiments, the wireless devices are selected from the group consisting of mobile/cellular telephones (e.g., smart devices, e.g., smartphones), tablets, desktop computers, laptop computers, notebook computers, and medical equipment (e.g., medical devices used in the treatment, prevention, and diagnosis of a patient). In certain embodiments, the identity of the medical equipment that is capable of wireless transmission is also maintained in the central registry as a credentialed user.

The methods of precision professional health-related (PHR) communication provide for interfacing with one or more credentialed users through an interfacing tool, e.g., on a server. The interfacing tools of the present invention are user interfaces for providing precision professional health-related (PHR) communication, e.g., graphical user interfaces (GUI), which are user-facing for interacting with a credentialed user to transmit information, collect information, as well as act on that information through combination, analysis, and ultimately providing diagnostic analysis through precision PHR communication. In particular embodiments, such interface may comprise interface components/modules such as buttons, drop-down menus, drop-down lists, entry blanks, links to prior stored information, and text for: instruction, request, or stored information. Moreover, such interface components/modules and list members, e.g., healthcare workers or patient names, may be updated/modified (e.g., by an administrator of the interface or in an automated fashion by reference to separate listing held outside the interface, e.g., in the EMR system).

In certain embodiments of the invention, the interface visualization may provide for depicting timelines, e.g., in landscape view, with several parallel processes.

In certain embodiments of the invention, the interface may be patient centered to establish optimal team involvement.

In certain embodiments of the invention, the interface visualization may provide for visualizing team members availability at a given time (e.g., which may be engaged automatically). In particular embodiments, such visualization may be filtered by time and team member.

In certain embodiments of the invention, the step of interfacing with the healthcare information system of the host healthcare institution comprises authentication of the credentialed user for accessing the communication interface. In certain embodiments, to access the precision architecture control structure (PACS), the credentialed user may first download an app, or access a web browser or web portal. In particular embodiments, registration or authentication (e.g., single or multi factor authentication, e.g., signing in via password) is required prior to utilization of the precision professional health-related (PHR) communication interface. In particular embodiments, the user registers with an administrator of the healthcare information system of the host healthcare institution, e.g., creating a unique interface with a particular encryption key.

In certain embodiments of the invention, the step of interfacing with the healthcare information system of the host healthcare institution comprises creation of a patient specific storage path, e.g., incident specific storage path, e.g., injury specific storage path, to collect the professional health-related (PHR) data (e.g., structured dialogs) from a user, e.g., credentialed user. In particular embodiments, the patient specific storage path is based on the healthcare worker. In specific embodiments, the patient specific storage path is based on a team of healthcare workers.

In certain embodiments of the invention, the step of interfacing with the healthcare information system of the host healthcare institution comprises reestablishing interface with an existing patient specific storage path to collect additional data, e.g., PHR data, e.g., structured dialogs. In particular embodiments, the existing patient specific storage path is based on the healthcare worker. In specific embodiments, the existing patient specific storage path is based on the incident. In certain embodiments, the existing patient specific storage path is created by the healthcare worker. In certain embodiments, the existing patient specific storage path is created by the administrator of the communication interface, e.g., based on credentialed users and structured dialogs.

In certain embodiments of the invention, the one or more wireless devices interfacing with the healthcare information system of a host healthcare institution also interfaces with one or more additional healthcare information systems (e.g., wherein the first is a hospital healthcare information system and the second is a physician office healthcare information system.

i. Precision Architecture Control Structure (PACS)

The precision architecture control structure (PACS) of the present invention comprises professional health-related (PHR) structured dialogs suitable for precise clinical diagnosis, including in certain embodiments, for example, clinical treatment options. In particular, the present invention provides methods, tools, and systems using precision architecture control structure (PACS) comprising professional health-related (PHR) structured dialogs suitable for precise clinical diagnosis, in combination with encrypted transmission which is capable of HIPAA compliant communication of a healthcare information system with a credentialed user. The increased clinical precision of these tools, systems, and related methods affords greater efficiency in clinical treatment that is translated into increased safety in patient care.

The PACS of the present invention comprises a database of structured dialog alternatives that afford unique precision to PHR communication among credentialed users using discrete level messaging, aggregate level messaging, and super-aggregate messaging. The precision of the structured dialogs derives, at its core, from discrete level messaging directed to primitive events and the standardized precise capture/representation of those events through selection from a pre-identified database listing. Discrete level messaging includes, but is not limited to, the capture of basic analytical dialogs and data entry for measurements, observations, and other data points that instruct the credentialed user precisely on basic analytical data useful for developing a diagnosis. Discrete level messaging aggregation may be utilized to advance the structured dialog progression in a given dialog resulting in aggregate level messaging. Aggregate level messaging introduces more advanced analytical considerations into the structured dialogs, as well as certain basic diagnoses. In particular embodiments, predictive learning (e.g., with artificial intelligence, e.g., using analytical analysis to accurately determine outliers) may be used to aggregate the discrete level messaging of the PACS to result in aggregate level messaging. In certain further embodiments, the aggregate level messaging is further aggregated to advance the structured dialog progression in a given dialog resulting in super-aggregate level messaging. Such super-aggregate level messaging is directed to a diagnosis based on both discrete level messaging and aggregate level messaging.

In certain embodiments of the PACS of the present invention, medical equipment may produce discrete level messaging, for example, patient thermometer measurements. Such patient measurements may be transmitted manually or through automated means from the medical equipment registered as a credentialed user, as a structured dialog comprising the discrete level messaging to a credentialed user (e.g., a person or medical equipment registered as a credentialed user) and/or recorded in a database, e.g., an EMR system (e.g., for diagnostic or administrative purposes such as billing). In certain embodiments, the structured dialog is first passed to the healthcare information system of the host healthcare institution and then passed to the credentialed user, e.g., wherein the healthcare institution may be used as the intermediary gate of structured dialogs (e.g., which may, in turn, be used to parse relevant information to and from the EMR). In particular embodiments, the discrete level messaging may be logged into a relational database designed to establish follow-up action or for combination with other discrete level messaging, resulting in aggregate level diagnosis and super-aggregate level diagnosis (i.e., from the combination of aggregate level messaging in the same platform), for example, via automation. In specific embodiments, the automated detection of a diagnosis may be used for triage purposes, e.g., generating a warning, e.g., a critical warning. In certain specific embodiments, the prioritization of the messaging may be defined by hospital policies and provider specific requirement.

In certain embodiments of the PACS of the present invention, the discrete, aggregate, and super-aggregate messaging of the structured dialogs may be grouped with color coded changes, e.g., progressive color coded changes. For example, color changes may depict the urgency of the response time or perhaps are defined by the hospital, e.g., based on in-house progression system. In particular embodiments the PACS of the present invention may be presented through additional characterization (other than by color) for color blind users, for example, through utilization of different shapes instead of color (e.g., hospital specific), e.g., 1 to 3 stars or traveling star shape.

In certain embodiments the structured dialogs are presented in a manner that the credentialed user may select from a list (e.g., a pop-up list, a checklist, a scrolling list, a drop-down list, any other iteration of generated list, for example, known in the state of art). For example, when a credentialed user, such as an individual healthcare worker, wishes to transmit a PHR communication, a private application is launched on a suitable mobile device, e.g., a smart device, e.g., smartphone, which presents a user interface that allows the simple and rapid assembly of a PHR communication by presenting a list of options to engage in structured dialog.

In certain embodiments of the PACS of the present invention, the PACS comprises an interface feature allowing the ability of the credentialed user to enter any text, i.e., "free text." In particular embodiments, the PACS further comprises the step of screening and/or auditing this additional free text for HIPAA-sensitive content. In particular embodiments, the PACS further comprises the step of screening and/or auditing this additional free text for relation to existing/stored structured dialog options, i.e., mapping the free text language to existing structured dialog. Moreover, stored free text, e.g., maintained by the healthcare information system, creates an opportunity to iteratively refine the menu of available structured dialog options. An alternative embodiment provides each credentialed user, e.g., a healthcare worker, the ability to update/customize a personal registry of structured dialog messages in the healthcare information system of the host healthcare institution. In specific embodiments, the healthcare information system of the host healthcare institution distributes to every credentialed user the updated/customized structured dialog entered by other credentialed users, e.g., through a centralization of the structured dialog options (e.g., as either encrypted or unencrypted). In specific embodiments, free text may be entered using voice recognition input, for increased speed/efficiency. Moreover, in additional embodiments, the PACS may be analyzed for free text to characterize compliance with the precision aspects of the invention, e.g., in real-time. In specific embodiments, the interface may provide a report on the provider or team member related to this analysis, e.g., to optimize utilization of structured dialogs by team members (e.g., in a feedback loop, e.g., infinite loop).

In certain embodiments of the present invention, recognition of repetitive activity, structured dialogs, and/or free text may be used to optimize routine tasks, e.g., across all users or for an individual user. In particular embodiments, repetitive activity, structured dialogs, and free text may be analyzed in real time to provide improved interfacing with an individual user.

In certain embodiments of the PACS of the present invention, the PACS provides the opportunity to record free text, e.g., in a dialog entry box. In certain embodiments, the PACS provides dialog anticipation text for offering suggestions to the credentialed user. In particular embodiments, the predictive anticipation aligns/maps the free text to a structured dialog.

B. Establishing One or More Registries of Credentialed Users,

Another step of the methods of precision professional health-related (PHR) communication of the present invention comprises establishing one or more registries of credentialed users. Credentialed users may be selected from the group consisting of healthcare workers, patients e.g., active patients, medical equipment, and any combination thereof. Such healthcare workers are medical professionals (e.g., doctor, nurse, pharmacist, etc.) suitable for collecting, distributing, and receiving PHR data/information.

In certain embodiments of the present invention, the credentialed user is selected from medical equipment, a healthcare worker, or an active patient.

In certain embodiments of the present invention, the credentialed user is selected from a healthcare worker or an active patient.

In certain embodiments of the present invention, the credentialed user is selected from medical equipment. In particular embodiments, the medical equipment is selected from machines included from but not limited to generating patient specific physiological data, hospital medical equipment, and hospital ancillary equipment. Such equipment is capable of generating discrete level messaging, aggregate level messaging, and super-aggregate messaging. Discrete level messaging includes status information related to the machine, availability and resource allocation/identification including equipment, personnel, and diagnostic resources. In specific embodiments, the medical equipment is capable of interfacing with the Internet of Things.

In certain embodiments of the present invention, the host healthcare institution maintains the central registry of credentialed users. In certain embodiments, each credentialed user is assigned a code reference related to encryption keys, and therefore provided access to the professional health-related communication/information. In particular embodiments, the host healthcare institution distributes an application to the smart phones assigned to each health care worker.

In certain embodiments of the present invention, the healthcare worker (e.g., doctors and/or registered nurses) is assigned, e.g., as a team, to a patient. In certain embodiments, this team roster may be assigned upon creation of a patient registry listing. In certain embodiments, this team roster may be assigned/presented at time of communication, e.g., structured dialog creation, to define message recipient(s), and can optionally accommodate cross-coverage relationships. Also, the history of the care team membership roster can be stored, e.g., to determine who is on a previous shift or on next shift.

In certain embodiments of the registry, each patient has an associated table specifying, for example: Patient ID (e.g., name, MR number, and current location such as inpatient bed or outpatient status); family members; contact phone numbers of patient and family; health care team including PCP; specialists; nurses; respiratory therapy; physical therapy; occupational therapy; speech therapy; and possible: med reconciliation list.

In certain embodiment of the invention, the registry of credentialed users is stored on the healthcare information system of the host healthcare institution (e.g., capable of access or modification).

In certain embodiment of the invention, the registry of credentialed users is stored on a machine readable medium, e.g., server, separate from the healthcare information system of the host healthcare institution (e.g., capable of access or modification).

In certain embodiments, to access the precision architecture control structure (PACS), the credentialed user may first download an app, or access a web browser or web portal. In particular embodiments, registration or authentication (e.g., single or multi factor authentication, e.g., signing in via password) is required prior to utilization of the precision professional health-related (PHR) communication interface. In particular embodiments, the user registers with an administrator of the healthcare information system of the host healthcare institution, e.g., creating a unique interface with a particular encryption key.

C. Assigning Encryption Key to Each User for Use in Encryption and Decryption

In another step of the methods of precision professional health-related (PHR) communication of the present invention, the method comprises assigning an encryption key to each user for use in both encryption and decryption. Such encryption affords HIPAA compliance to these methods. In certain embodiments, encryption provides a multi-tiered distributed HIPAA-compliant asymmetric encryption method.

Encryption keys are designed with algorithms intended to ensure that every key is unpredictable and unique, e.g., a random string of bits created explicitly for scrambling and unscrambling data. Asymmetric encryption is a form of encryption where keys come in pairs. In certain embodiments, the keys are interchangeable, in the sense that if key 1 encrypts a message, then 2 can decrypt it, and if key 2 encrypts a message, then key 1 can decrypt it. Asymmetric cryptography, also known as public key cryptography, uses public and private keys to encrypt and decrypt data. The keys are simply large numbers that have been paired together but are not identical (asymmetric). One key in the pair can be shared with everyone, and it is called the public key. Moreover, upon assignment of an encryption key to a user, PHR communications may be transmitted using non-secure communication channels, such as SMS.

In certain embodiments of the invention, assigning an encryption key to each user utilizes a public-key asymmetric encryption algorithm. In particular embodiments, the healthcare information system transmits to the smart device, e.g., smartphone, application an encrypted list of healthcare worker names and randomly-assigned health care worker code numbers.

In certain embodiments of the invention, assigning an encryption key to each user utilizes a public-key asymmetric encryption algorithm. In particular embodiments, the healthcare information system transmits to the smart device, e.g., smartphone, application, in a HIPPA-compliant fashion, an encrypted list of patient names and randomly-assigned patient code numbers.

In certain embodiments of the invention, assigning an encryption key to each user utilizes a public-key asymmetric encryption algorithm, wherein the structured dialogs are encrypted before transmission by healthcare information system of the host healthcare institution to the smart device, e.g., smartphone, application together with randomly assigned code numbers.

D. Encrypting PHR Structured Dialog Prior to Transmission to Wireless Devices of Defined User with Assigned Encryption Key In another step of the methods of precision professional health-related (PHR) communication of the present invention, the method comprises encrypting the PHR structured dialog prior to transmission to said wireless devices of a defined user with an assigned encryption key. Applying the encryption key to the transmission of each user, prior to the transmission, affords the ability to transmit the communication using non-secure, open communication channels, such as SMS (i.e., as the random numbers assigned by the encryption to the recipient, the patient and the structured dialog cannot be understood by direct inspection). In particular embodiments, free text used, e.g., in addition to the structured dialogs, is also encrypted using the same encryption process.

Further, certain embodiments of the methods of the invention provide for analysis of the communication for HIPAA protected content. In particular embodiments, communication of information that is not HIPAA protected may occur over open channel without encryption (e.g., unless HIPAA characterized information is communicated, such as patient ID or patient related data, subjecting all communication to be considered as part of the medical records).

In certain embodiments of the invention, the encryption is achieved by using a public-key asymmetric encryption algorithm with computing resource needs such that the major computing burden is placed on the encryption process and a minor computing burden is placed on the decryption process.

E. Receiving Encrypted PHR Structured Dialog at Wireless Device Assigned to User Another step of the methods of precision professional health-related (PHR) communication of the present invention, the method comprises receiving the encrypted PHR structured dialog at said wireless device assigned to said user, e.g., healthcare worker. When the PHR structured dialog is received by the smart device, e.g., smartphone, assigned to the 'destination' healthcare worker, the private application converts the coded PHR structured dialog by substituting plain-text for the coded messages using a decryption key, thereby revealing the full intended message. The coded, or encrypted, structured dialog may be received via non-secure communication channels, e.g., SMS; which may then be imported by the smart device, e.g., smartphone, communication interface for action by the communication interface.

In certain embodiments of the present invention, the encrypted PHR structured dialog is decrypted into user viewable information, e.g., plain-text, thereby revealing the full intended structured dialog.

In certain embodiments of the present invention, the encrypted PHR structured dialog is decrypted to create a medical history log, e.g., in an EMR.

In certain embodiments of the present invention, the encrypted PHR structured dialog is decrypted to initiate an automated aggregate level (or super-aggregate level) response action, e.g., creating a warning response. Such response may include, for example, scheduling actions to make efficient use of resources. In particular embodiments, such warnings may be captured to identify trends and afford predictive needs for medical equipment.

In certain embodiments, the receipt of the encrypted PHR structured dialog at said wireless device assigned to the user begins a response period that may be defined/classified as non-urgent or urgent. Such definition/classification may assist in the act of triage of a patient condition. In certain embodiments, the communication may require an instant response. In particular embodiments, the importance and urgency may be reflected using measures selected from the group consisting of a countdown, visual field within messaging system, availability to the healthcare worker/team until completion, and any combination thereof. For example, importance and urgency may be reflected by implementation of flag system for priority and visual confirmation with default halt and switch to cross coverage if progression of non-responded and unconfirmed messages reaches a critical hospital specific number, and/or other set parameters and criteria are not met.

IV. Precision Professional Health-Related (PHR) Communication System of the Invention The precision professional health-related (PHR) communication interfaces of the present invention, described herein, may be incorporated into systems, which may also comprise a healthcare information system, and one or more wireless devices.

As such, another embodiment of the present invention provides a precision professional health-related (PHR) communication system suitable for protecting the confidentiality and security of healthcare information within a host healthcare institution comprising:

a healthcare information system (e.g., on a machine-readable medium, e.g., a server);

one or more wireless devices (e.g., smart devices, e.g., smartphones); and a precision professional health-related (PHR) communication interface comprising a machine-readable medium having instructions stored thereon for execution by a processor to perform a method comprising the steps of:

interfacing with the healthcare information system of a host healthcare institution with one or more wireless devices using precision architecture control structure (PACS) comprising professional health-related (PHR) structured dialogs suitable for precise clinical diagnosis;

establishing one or more registries of credentialed users, e.g., credentialed health care workers and active patients;

assigning an encryption key to each user for use in both encryption and decryption, e.g., asymmetric encryption (and decryption);

encrypting the PHR structured dialog prior to transmission to said wireless devices of a defined user with an assigned encryption key, e.g., using a public-key asymmetric encryption; and receiving the encrypted PHR structured dialog at said wireless device assigned to said user (e.g., health care worker, wherein the encrypted PHR structured dialog is decrypted into user viewable information, e.g., plain-text, thereby revealing the full intended structured dialog), such that the healthcare information system of the host healthcare institution is capable of communicating with one or more of said users by precision professional health-related (PHR) communication;

providing a precision communication system suitable for protecting the confidentiality and security of the professional health-related (PHR) information within the host healthcare institution.

V. Design Aspects of the Invention

Independent of the utility related to precision professional health-related (PHR) communication interface of the present invention, the ornamental appearance of any novel design provided herein is intended to be part of this invention, for example, each of the perspective views in FIGS. 3 through 8, which may form an independent or combined ornamental appearance of precision professional health-related (PHR) communication interfaces described herein.

Accordingly, one embodiment of the present invention provide an ornamental design for a precision professional health-related (PHR) communication interface as shown and described.

EXEMPLIFICATION

Having thus described the invention in general terms, reference will now be made to the accompanying drawings of exemplary embodiments, which are not necessarily drawn to scale, and which are not intended to be limiting in any way.

In this respect, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

FIG. 1 depicts a schematic representation of the architecture of the core executed processes of one particular embodiment of the precision professional health-related (PHR) communication systems of the present invention. The wireless device, e.g., the smart device, e.g., smartphone, or PDA assigned to an individual healthcare worker, interfaces with a host hospital healthcare information system (HIS) and a host physician office healthcare information system (HIS) through a precision professional health-related (PHR) communication interface of the present invention. The transmission of the structured dialogs between the wireless device and each HIS, and vice versa, may occur via a completely encrypted channel (e.g., secured land lines and encrypted wireless links) or via an open channel (e.g., secured land lines and open wireless links).

Figure 2:
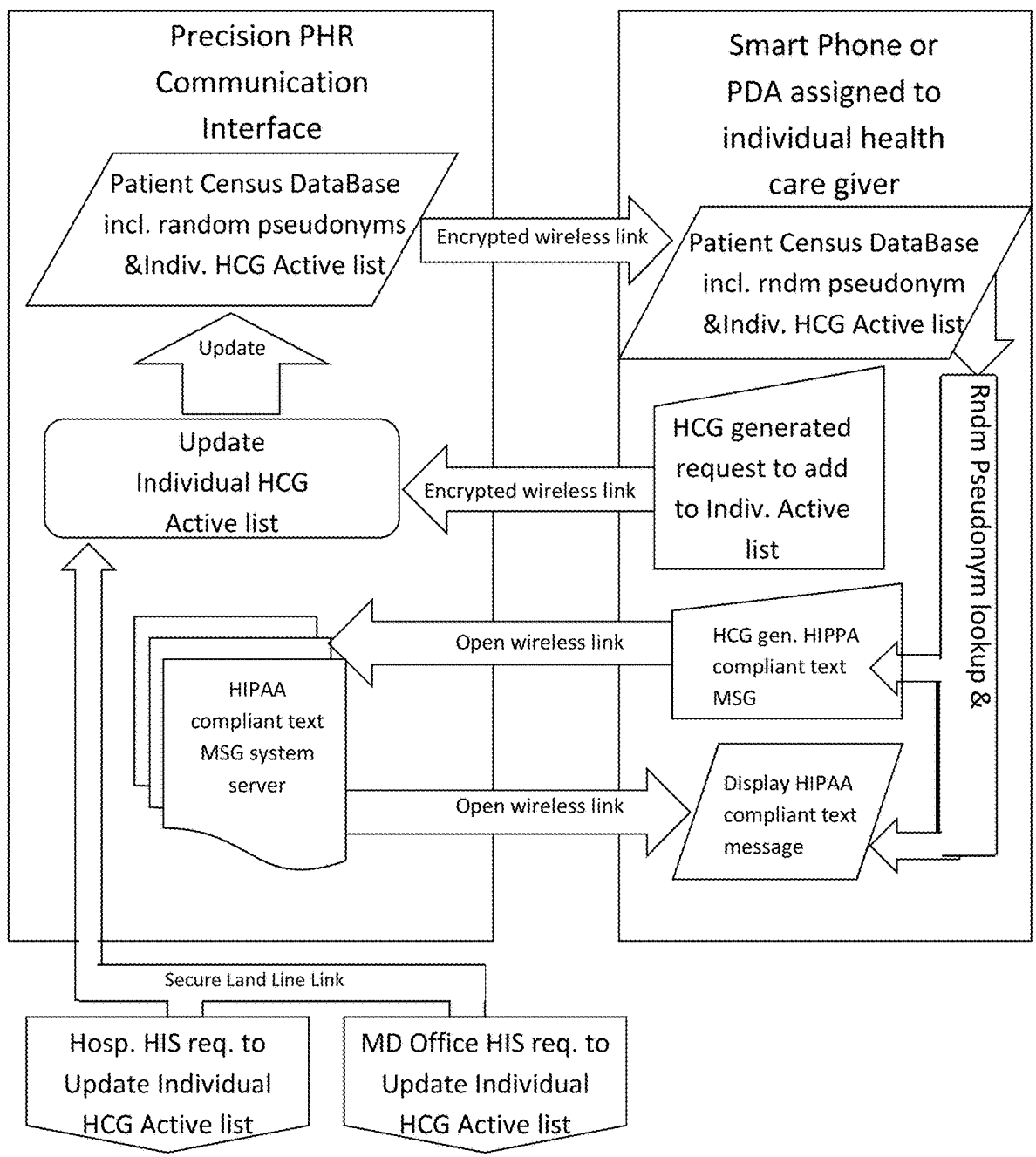
FIG. 2 depicts a schematic representation of one particular embodiment of the architecture of the precision professional health-related (PHR) communication systems of FIG. 1.

FIG. 2 depicts a schematic representation of one particular embodiment of the architecture of the precision professional health-related (PHR) communication systems of FIG. 1. The schematic representation depicts specific interfacing between the wireless device, e.g., the smart device, e.g., smartphone, or PDA assigned to an individual healthcare worker, and a precision professional health-related (PHR) communication interface of the present invention, wherein such communication reflects the addition of an active patient to the list stored/accessible in the precision professional health-related (PHR) communication interface. Such addition may occur by addition from the wireless device sending a request to the precision PHR communication interface or from either of the healthcare information systems (HIS). The active patient list may be used to generate HIPAA compliant structured dialogs that are transmitted via open channel communication through SMS messaging after encryption (e.g., producing encryption 'pseudonyms' for each patient), and received for decryption by the counterpart.

Figure 3:
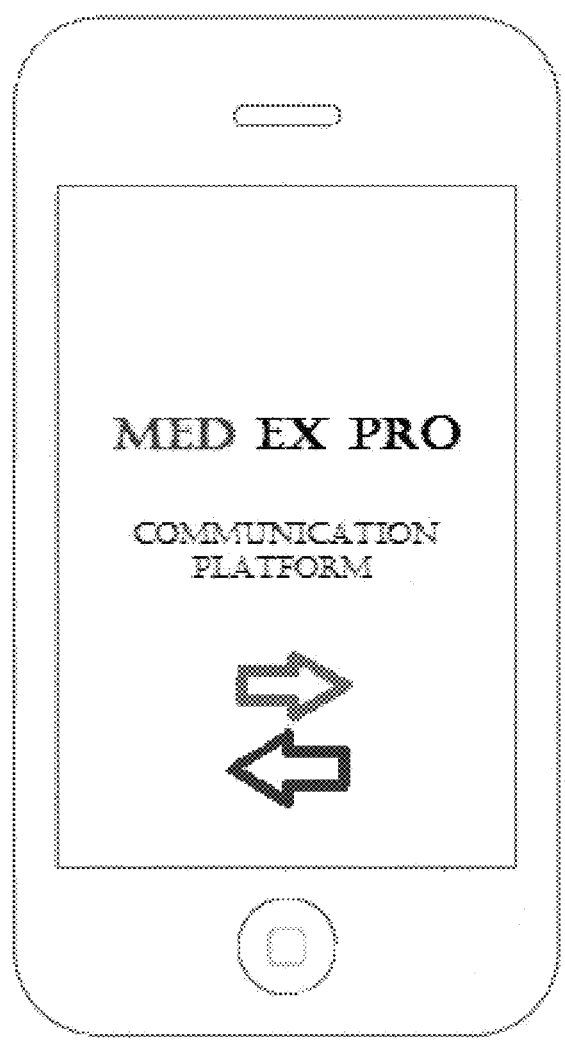
FIG. 3 depicts one embodiment of the introductory screen of the graphical user interface of the precision professional health-related (PHR) communication interfaces of the present invention.

FIG. 3 depicts one embodiment of the introductory screen of the graphical user interface of the precision professional health-related (PHR) communication interfaces of the present invention. No user action is necessary related to this screen. In certain embodiments, the screen automatically transitions into the home screen after a brief delay, e.g., 0.5 second.

Figure 4:
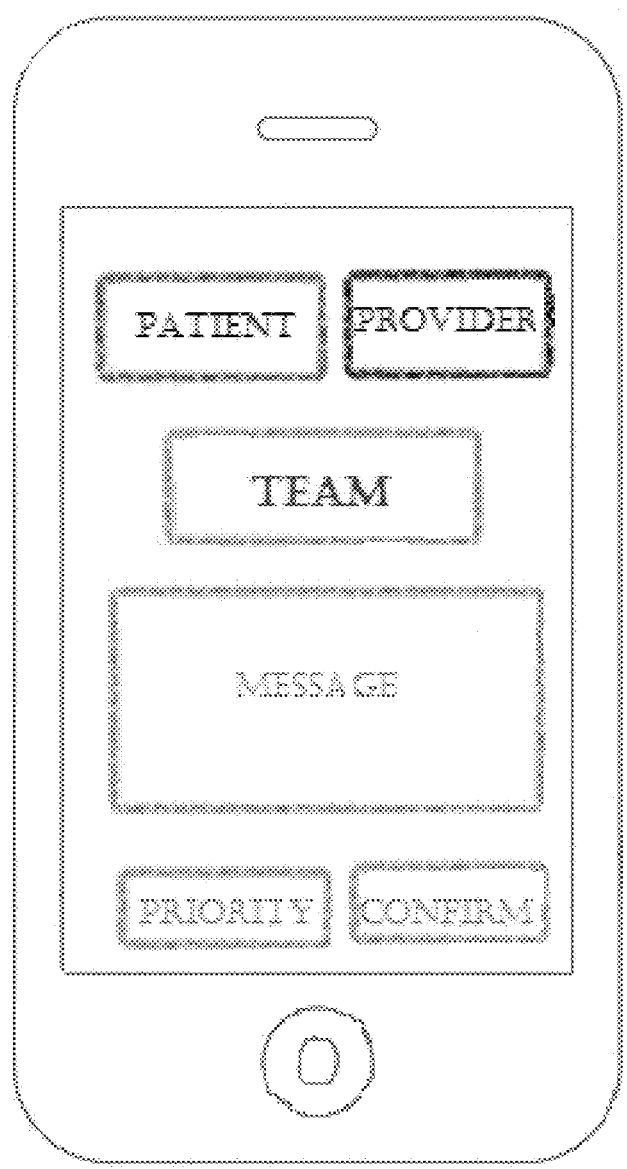
FIG. 4 depicts one embodiment of the patient selection screen of the graphical user interface of the precision professional health-related (PHR) communication interfaces of the present invention.

FIG. 4 depicts one embodiment of the patient selection screen of the graphical user interface of the precision professional health-related (PHR) communication interfaces of the present invention. The clickable PATIENT button affords transition to a HIPAA compliant patient selection screen. The clickable PROVIDER button affords transition to the provider selection screen. The clickable TEAM button affords transition to a team selection screen. The clickable MESSAGE button affords transition to a message composition screen, e.g., via a new screen, expansion of the message area, or compressing other screen areas or buttons. The clickable PRIORITY button affords transition to an established priority screen, e.g., via new screen or replacement of the button with 3 smaller buttons. The clickable CONFIRM button sends the structured dialog (including any free text) as encrypted message through secure or non-secure communication channels. The recipient user, e.g., provider or team, of the structured dialog may provide confirmation in a recipient confirmation screen, which may also afford the recipient an opportunity to send a message, e.g., structured dialog or free text.

Figure 5:
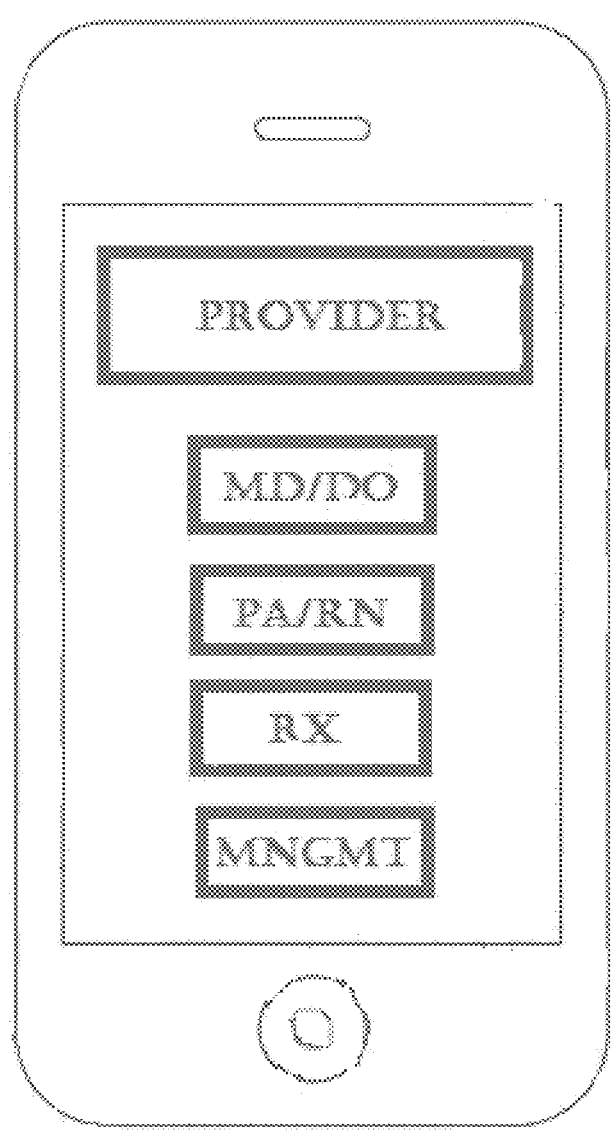
FIG. 5 depicts one embodiment of the provider selection screen of the graphical user interface of the precision professional health-related (PHR) communication interfaces of the present invention.

The patient selection screen may comprise buttons, such as patient list, contact information (including, for example, demographics, phone, email, etc), and a button that allows the entry of a new patient. Further, the provider selection screen may comprise similar/related buttons. FIG. 5 depicts one embodiment of the provider selection screen of the graphical user interface of the precision professional health-related (PHR) communication interfaces of the present invention. This provider selection screen may comprise buttons that delimit the provider selected from MD/DO, PA/RN, RX, MNGMT. Team selection screens may follow a similar structure as the provider selection screen of FIG. 5, and which may also include additional buttons on the same or different related screens, such as a button that allows the entry of a new team.

Figure 6:
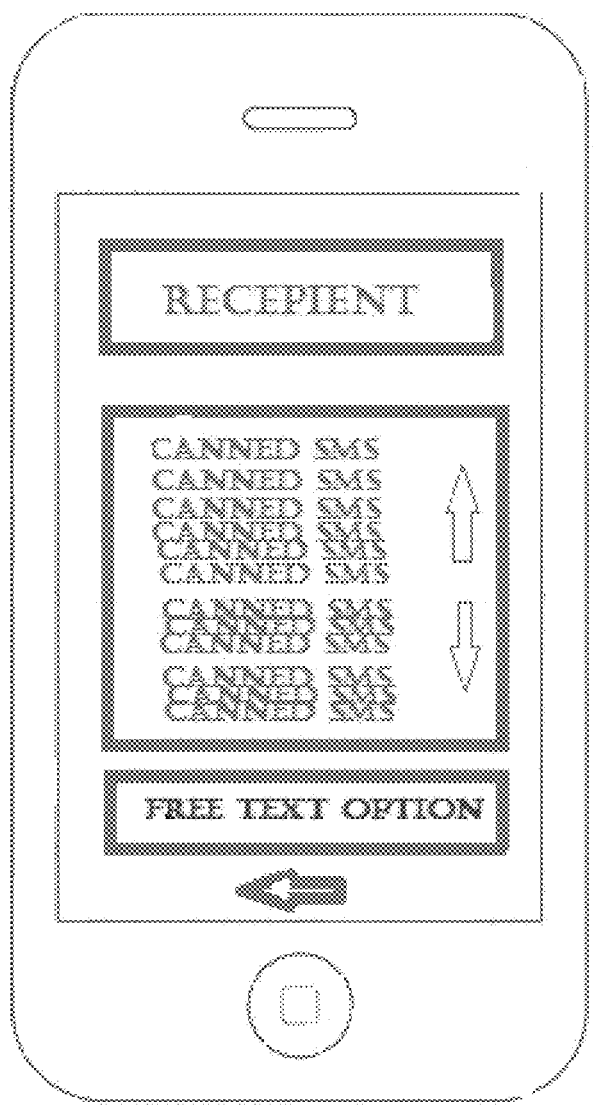
FIG. 6 depicts one embodiment of the message composition screen of the graphical user interface of the precision professional health-related (PHR) communication interfaces of the present invention, wherein structured dialogs are represented here as "canned messages."

FIG. 6 depicts one embodiment of the message composition screen of the graphical user interface of the precision professional health-related (PHR) communication interfaces of the present invention, wherein structured dialogs are represented here as "canned messages." The message composition screen may comprise a button for selection of the RECIPIENT, a selection area for selecting the structured dialog, and a FREE TEXT OPTION button to transition to a free text selection screen. Another message composition screen may comprise a larger space for free text entry, and a button to transition to a structured dialog selection screen. A prior screen button may also be present, e.g., as an arrow image pointing to the left.

Figure 7:
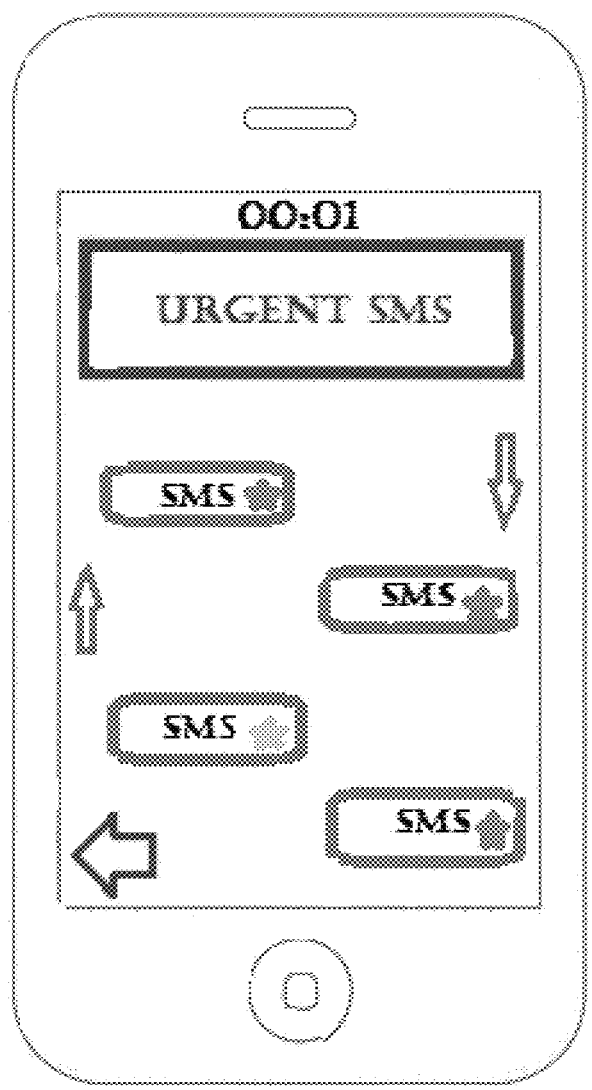
FIG. 7 depicts one embodiment of the priority structure screen of the graphical user interface of the precision professional health-related (PHR) communication interfaces of the present invention.

FIG. 7 depicts one embodiment of the priority structure screen of the graphical user interface of the precision professional health-related (PHR) communication interfaces of the present invention. In certain embodiments, the URGENT SMS button remains on top of the screen, e.g., with a countdown timer. Other prioritized SMS buttons may be referenced with different colors, e.g., using stars, related to importance. A prior screen button may also be present, e.g., as an arrow image pointing to the left.

Figure 8:
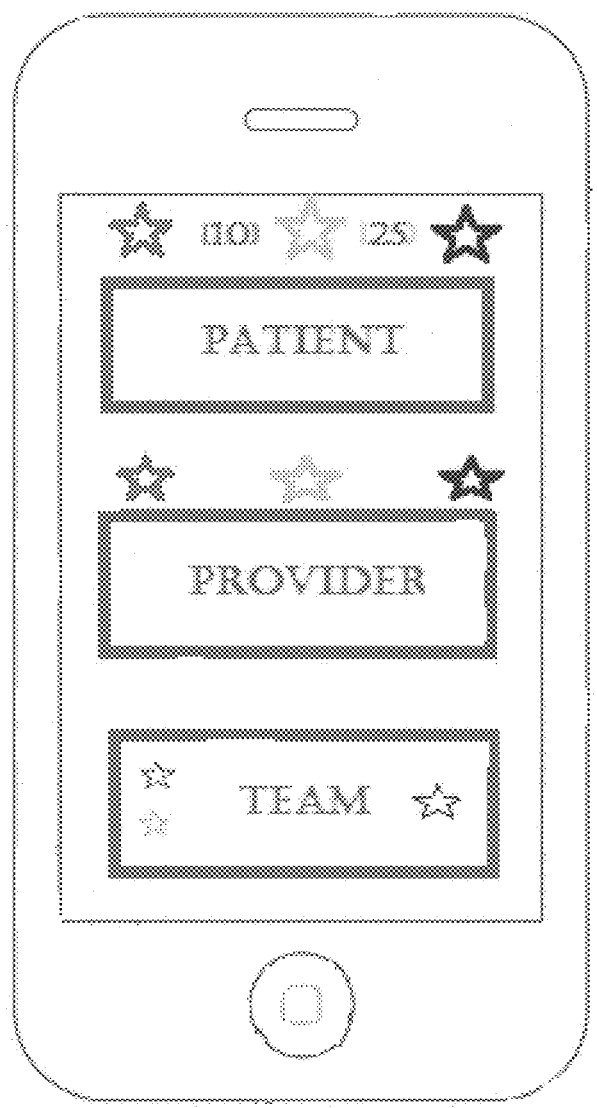
FIG. 8 depicts one embodiment of the SMS tracking screen of the graphical user interface of the precision professional health-related (PHR) communication interfaces of the present invention.

FIG. 8 depicts one embodiment of the SMS tracking screen of the graphical user interface of the precision professional health-related (PHR) communication interfaces of the present invention. The screen comprises PATIENT, PROVIDER, and TEAM buttons with indications of messages received, and may further include breakdown by priority. Each button may further transition to a screen directed solely to the patient, provider, or team, respectively.

Example 1

Exemplary/Sample Structured Dialogs within the Scope of the Present Invention

The precision architecture control structure (PACS) of the present invention comprises professional health-related (PHR) structured dialogs suitable for precise clinical diagnosis, This clinically effective medical communication through efficient distillation of clinically relevant standardized content affords greater efficiency in clinical treatment that is translated into increased safety in patient care.

The following examples of sample structured dialogs are shown for demonstration purposes only, and are not intended to limit the invention in any way:

Sample Structured Dialog from Doctor to Doctor:
  A. Please see XXXXX, MR #QQQQ in consult as inpt in room YYY on a ZZZ basis. Diagnosis is DDDDDD.
    1. Received your message
    2. Will do. Thanks
    3. Please call me about this
    4. May I call you now?
       a) yes
       b) better at TTTTTT
    5. may I call you back at TTTTT?
  B. I have evaluated patient XXXXXXX
    1 Please call me
    2. May I call you now?
       a) yes
       b) better at TTTTTT 3. May I call you back at TTTTT?
4. Can I meet you at the bedside of XXXXXXX [at time {now,:TTTTTT}]
   a) Time UUUUU works for me.
C. Please call me about XXXXX, MR #QQQQ in consult as inpt in room YYY on a ZZZ basis. Diagnosis is DDDDDD.
1. Received your message
2. Will do. Thanks
3. Please call me about this
4. May I call you now?
   a) yes
   b) better at TTTTTT
5. May I call you back at TTTTT?

Sample Structured Dialog from Doctor to Nurse
A. Please call me about patient XXXXXX. My phone number is NNN-NNN-NNNN
B. What is the AAAA, BBBB, CCCC, of patient XXXXXXXX?
C. Has pt XXXXXXX left the floor yet to go to KKKKKKK
D. Has pt XXXXXXXX had their FREETEXT taken care of yet?

Sample Structured Dialog from Nurse to Doctor
A. Pt XXXXXX has had a change in clinical status [consisting of {change in mental status; chest pain; Shortness of breath; bleeding; abdominal pain; pain}]

Sample Structured Dialog from Office Staff to Doctor
A. Please see XXXXX, MR #QQQQ in consult as inpt in room YYY on a ZZZ basis. Diagnosis is DDDDDD. Referring MD is MMMMMMM.
1. Please call Sample Structured Dialog from Doctor to Office Staff
A. I'm running late. [I'll be there in TTTTTTT]
1. OK
2. Please call [STAT; ASAP; When you are able]
B. On pt PPPPPPPP I just performed service SSSSSSSSS.
C. I need family contact information for pt PPPPPPPPP
D. I need Care team contact information on pt PPPPPP
E. I need contact information for doctor MMMMMMM
F. What is my calendar for the [current;next; DDDD] [day;week;month]

Sample Structured Dialog from Office Staff to Patient
A. The doctor is running late. We estimate that you will be seen at TTTTTT.
B. Please call the office regarding BBBBBBBB [direct phone number NNN-NNN-NNNNN].
C. A reminder from the office of Dr. DDDD: You have an appointment on YYYYY at time TTTTTT at Address AAAAAAAA. Please remember to bring your WWWWW
D. A reminder from the office of Dr. DDDD: You have an appointment on YYYYY at time TTTTTT at Address AAAAAAAA to have a test LLLLLLL performed. [Please remember to eat or drink nothing after TTTTTTT]
E. Preoperative and pretest instructions
F. Post operative and posttest instructions Sample Structured Dialog from Patient to Office Staff
A. What is the result of my QQQQQQ
B. I need a refill on my MMMMMM
C. Please have the nurse call me [ASAP, today, when you are able].
D. Please call me concerning a billing question.

Sample Structured Dialog from Pharmacy to Patient
A. Your prescription will be ready for pickup at QQQQQ. Please pick this up by TTTTT.
1. Thank you. I will be there[by {time TTTTT;today; tomorrow}]
2. Thank you. YYYYY will be there[by {time TTTTT; today;tomorrow}]

Sample Structured Dialog from Pharmacy to Doctor
A. Please call us concerning pt XXXXXXX. Return number direct to pharmacist is NNN-NNN-NNNN Sample Structured Dialog from Patient to Pharmacy
A. Is my prescription ready?
B. Can I refill my prescription for {med A; Med B; Med C} or do I need to get an updated prescription from my doctor?
C. I have a question. Can the pharmacist call me?

Additional sample structured dialogs may be understood in this light from Administration to Clinical Staff, from Nurse to Nurse, from Clinical Staff to Administration, from Doctor to Patient, and from Patient to Doctor.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:
1. A system comprising:
   a healthcare information system of a host healthcare institution;
   one or more wireless devices; and
   a professional health-related (PHR) communication user interface for use in interfacing between the healthcare information system and the one or more wireless devices, the PHR communication user interface comprising a machine-readable medium having instructions stored thereon for execution by a processor to perform a method comprising the steps of:
   the healthcare information system of the host healthcare institution interfacing with the one or more wireless devices using the PHR communication user interface providing PHR communication for interacting with one or more credentialed users;
   transmitting, collecting, and acting on medical communication utilizing a database listing of structured dialog alternatives comprised of discrete level messaging, aggregate level messaging, and super-aggregate messaging that afford medical PHR communication through distillation of clinically standardized content among the credentialed users, wherein
   the discrete level messaging is directed to primitive events and a standardized capture or representation of those events through selection from the alternatives of the structured dialog database listing;

the discrete level messaging is aggregated in an advancing of a structured dialog progression resulting in the aggregate level messaging that introduces more advanced analytical considerations into the structured dialogs and certain diagnoses; and the aggregate level messaging is aggregated in the advancing of the structured dialog progression resulting in the super-aggregate level messaging that is directed to a diagnosis based on both the discrete level messaging and the aggregate level messaging, such that the structured dialogs are suitable for clinical diagnosis affording medical PHR communication through distillation of clinically standardized content;

establishing one or more registries of the credentialed users;

assigning an encryption key to each credentialed user for use in both encryption and decryption;

encrypting the discrete level messaging, the aggregate level messaging, and the super aggregate level messaging of the credentialed user with the assigned encryption key prior to transmission to said one or more wireless devices from the healthcare information system of the host healthcare institution;

transmitting the encrypted discrete level messaging, the encrypted aggregate level messaging, and the encrypted super aggregate level messaging to said one or more wireless devices assigned to said credentialed user; and utilizing predictive learning in the advancing of the structured dialog progression, such that the healthcare information system of the host healthcare institution is capable of communicating with one or more of said users by PHR communication affording medical PHR communication between the healthcare information system of the host healthcare institution and the wireless devices through distillation of clinically standardized content.

2. The system of claim 1, wherein the transmission of the encrypted discrete level messaging, the encrypted aggregate level messaging, and the encrypted super aggregate level messaging occurs over open channel communication.

3. The system of claim 1, wherein the method further comprises the step of transmission of the encrypted discrete level messaging, the encrypted aggregate level messaging, and the encrypted super aggregate level messaging from said one or more wireless devices assigned to said credentialed user to the healthcare information system of the host healthcare institution.

4. The system of claim 3, wherein the transmission to the healthcare information system of the host healthcare institution occurs over open channel communication.

5. The system of claim 1, wherein the method further comprises the step of acknowledgement of receipt of the encrypted discrete level messaging, the encrypted aggregate level messaging, and the encrypted super aggregate level messaging.

6. The system of claim 1, wherein the method further comprises the step of storing the structured dialog, resulting in stored structured dialog data.

7. The system of claim 6, wherein the stored structured dialog forms part of an electronic medical records (EMR) system, affording access to the stored structured dialog data to both said credentialed users and a non-credentialed users.

8. The system of claim 1, wherein the method further comprises the step of utilizing haptic feedback to said credentialed user upon interfacing with the user interface.

9. The system of claim 1, wherein the machine-readable medium is selected from the group consisting of magnetic media, punched cards, paper tapes, optical disks, barcodes, magnetic ink characters, and solid state devices.

10. The system of claim 9, wherein the machine-readable medium is one or more network server disks.

11. The system of claim 1, wherein the PHR communication interface is suitable for protecting the confidentiality and security of the PHR information within the host healthcare institution.

12. The system of claim 1, comprising more than one healthcare information system.

13. A method of professional health-related (PHR) communication between a healthcare information system of a host healthcare institution and one or more wireless devices using a PHR communication user interface comprising the steps of:

the healthcare information system of a host healthcare institution interfacing with the one or more wireless devices using the PHR communication interface providing PHR communication for interacting with one or more credentialed users;

transmitting, collecting, and acting on clinically medical communication by utilizing a database listing of structured dialog alternatives in the PHR communication interface comprised of discrete level messaging, aggregate level messaging, and super-aggregate messaging that afford medical PHR communication through distillation of clinically standardized content among the credentialed users, wherein the discrete level messaging is directed to primitive events and a standardized capture or representation of those events through selection from the alternatives of the structured dialog database listing;

aggregating the discrete level messaging in an advancing of a structured dialog progression resulting in the aggregate level messaging that introduces more advanced analytical considerations into the structured dialogs and certain diagnoses; and aggregating the aggregate level messaging in the advancing of the structured dialog progression resulting in the super-aggregate level messaging that is directed to a diagnosis based on both the discrete level messaging and the aggregate level messaging, such that the structured dialogs are suitable for clinical diagnosis affording medical PHR communication through distillation of clinically standardized content;

the PHR communication interface establishing one or more registries of the credentialed users;

the PHR communication interface assigning an encryption key to each credentialed user for use in both encryption and decryption;

the PHR communication interface encrypting the discrete level messaging, the aggregate level messaging, and the super aggregate level messaging of the credentialed user with the assigned encryption key prior to transmission to said one or more wireless devices from the healthcare information system of the host healthcare institution;

the PHR communication interface transmitting the encrypted discrete level messaging, the encrypted aggregate level messaging, and the encrypted super aggregate level messaging to said one or more wireless devices assigned to said credentialed user; and the PHR communication interface utilizing predictive learning in the advancing of the structured dialog progression, such that the healthcare information system of the host healthcare institution is capable of communicating with one or more of said users by PHR communication affording medical PHR communication between the healthcare information system of the host healthcare institution and the wireless devices through distillation of clinically standardized content.

14. The method of claim 13, wherein the transmission of the encrypted discrete level messaging, the encrypted aggregate level messaging, and the encrypted super aggregate level messaging occurs over open channel communication.

15. The method of claim 13, wherein the method further comprises the step of transmission of the encrypted discrete level messaging, the encrypted aggregate level messaging, and the encrypted super aggregate level messaging from said wireless device assigned to said credentialed user to the healthcare information system of the host healthcare institution.

16. The method of claim 15, wherein the transmission to the healthcare information system of the host healthcare institution occurs over open channel communication.

17. The method of claim 13, wherein the method further comprises the step of acknowledgement of receipt of the encrypted discrete level messaging, the encrypted aggregate level messaging, and the encrypted super aggregate level messaging.

18. The method of claim 13, wherein the method further comprises the step of storing the structured dialog, resulting in stored structured dialog data.

19. The method of claim 18, wherein the stored structured dialog forms part of an electronic medical records (EMR) system, affording access to the stored structured dialog data to both said credentialed users and a non-credentialed users.

20. The method of claim 13, wherein the method further comprises the step of utilizing haptic feedback to said credentialed user upon interfacing with the user interface.

* * * * *